(12) United States Patent
Kanada

(10) Patent No.: US 11,756,292 B2
(45) Date of Patent: *Sep. 12, 2023

(54) SIMILARITY DETERMINATION APPARATUS, SIMILARITY DETERMINATION METHOD, AND SIMILARITY DETERMINATION PROGRAM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 278 days.

This patent is subject to a terminal disclaimer.

(21) Appl. No.: 17/327,772

(22) Filed: May 24, 2021

(65) Prior Publication Data

US 2021/0279920 A1 Sep. 9, 2021

Related U.S. Application Data

(63) Continuation of application No. PCT/JP2019/041478, filed on Oct. 23, 2019.

(30) Foreign Application Priority Data

Nov. 27, 2018 (JP) .................................. 2018-221166

(51) Int. Cl.
*G06V 10/82* (2022.01)
*G06T 11/00* (2006.01)
(Continued)

(52) U.S. Cl.
CPC .............. *G06V 10/82* (2022.01); *G06F 18/22* (2023.01); *G06T 11/005* (2013.01);
(Continued)

(58) Field of Classification Search
CPC ........... A61B 5/055; A61B 6/03; G06F 18/22; G06T 11/005; G06T 11/008;
(Continued)

(56) References Cited

U.S. PATENT DOCUMENTS 6,804,683 B1 10/2004 Matsuzaki et al.
8,009,936 B2 8/2011 Oosawa et al.
(Continued)

FOREIGN PATENT DOCUMENTS

JP 2000342558 12/2000
JP 2001155019 6/2001
(Continued)

OTHER PUBLICATIONS

"International Search Report (Form PCT/ISA/210) of PCT/JP2019/041478," dated Jan. 7, 2020, with English translation thereof, pp. 1-3.

(Continued)

*Primary Examiner* — Manuchehr Rahmjoo
(74) *Attorney, Agent, or Firm* — JCIPRNET

(57) ABSTRACT

A display control unit displays a tomographic image of a specific tomographic plane in a first medical image on a display unit. A finding classification unit classifies each pixel of a partial region of the first medical image into at least one finding. A feature amount calculation unit calculates a first feature amount for each finding in the partial region. A weighting coefficient setting unit sets a weighting coefficient indicating a degree of weighting, which varies depending on a size of each finding, for each finding. A similarity derivation unit performs a weighting operation for the first feature amount for each finding calculated in the partial region and a second feature amount for each finding calculated in a second medical image on the basis of the weighting coefficient to derive a similarity between the first medical image and the second medical image.

15 Claims, 16 Drawing Sheets

(51) Int. Cl.
*G06F 18/22* (2023.01)
*G06V 10/764* (2022.01)
*G06V 10/75* (2022.01)

(52) U.S. Cl.
CPC .......... *G06T 11/008* (2013.01); *G06V 10/764* (2022.01); *G06T 2207/10076* (2013.01); *G06T 2210/41* (2013.01); *G06V 10/759* (2022.01)

(58) Field of Classification Search
CPC ....... G06T 2207/10076; G06T 2210/41; G06T 7/00; G06V 10/759; G06V 10/764; G06V 10/82; G06V 2201/03; G06V 2201/12
See application file for complete search history.

(56) References Cited

U.S. PATENT DOCUMENTS

| | | | |
|---|---|---|---|
| 9,852,269 B2 * | 12/2017 | Sakagawa | ............... G16H 30/20 |
| 10,192,308 B2 | 1/2019 | Nakagomi | |
| 10,297,352 B2 | 5/2019 | Sakagawa et al. | |

FOREIGN PATENT DOCUMENTS

| | | |
|---|---|---|
| JP | 2008253292 | 10/2008 |
| JP | 2009095550 | 5/2009 |
| JP | 2011118543 | 6/2011 |
| JP | 2017189384 | 10/2017 |

OTHER PUBLICATIONS

"Written Opinion of the International Searching Authority (Form PCT/ISA/237) of PCT/JP2019/041478," dated Jan. 7, 2020, with English translation thereof, pp. 1-9.

Adrien Depeursinge et al., "Case-based lung image categorization and retrieval for interstitial lung diseases: clinical workflows", Int J CARS, vol. 7, Jun. 2011, pp. 97-110.

Joseph Jacob et al., "Evaluation of computer-based computer tomography stratification against outcome models in connective tissue disease-related interstitial lung disease: a patient outcome study", BMC Medicine, vol. 14, Nov. 2016, pp. 1-13.

Tae Iwasawa, "Quantitative evaluation of CT images of interstitial pneumonia by computer", Japanese Journal of Tomography, vol. 41, Aug. 2014, with English abstract, pp. 1-12.

"Office Action of Japan Counterpart Application" with English translation thereof, dated May 24, 2022, p. 1-p. 5.

* cited by examiner

FIG. 6

| TYPE OF FINDING | EVALUATION VALUE |
|---|---|
| INFILTRATIVE SHADOW | 2.9 |
| GROUND-GLASS SHADOW | 7.6 |
| RETICULAR SHADOW | 8.5 (MAXIMUM) |
| BRONCHODILATATION | 3.2 |
| . . . | . . . |
| . . . | . . . |
| NORMAL LUNG | −7.1 |
| LOW ABSORPTION AREA (EMPHYSEMA) | −12.3 |

FIG. 7

| TYPE OF FINDING | VOLUME |
|---|---|
| GROUND-GLASS SHADOW | 2050 |
| INFILTRATIVE SHADOW | 1400 |
| LOW ABSORPTION AREA | 361 |
| BRONCHODILATATION | 504 |
| RETICULAR SHADOW | 1210 |
| CYST | 180 |
| NORMAL LUNG | 1973 |

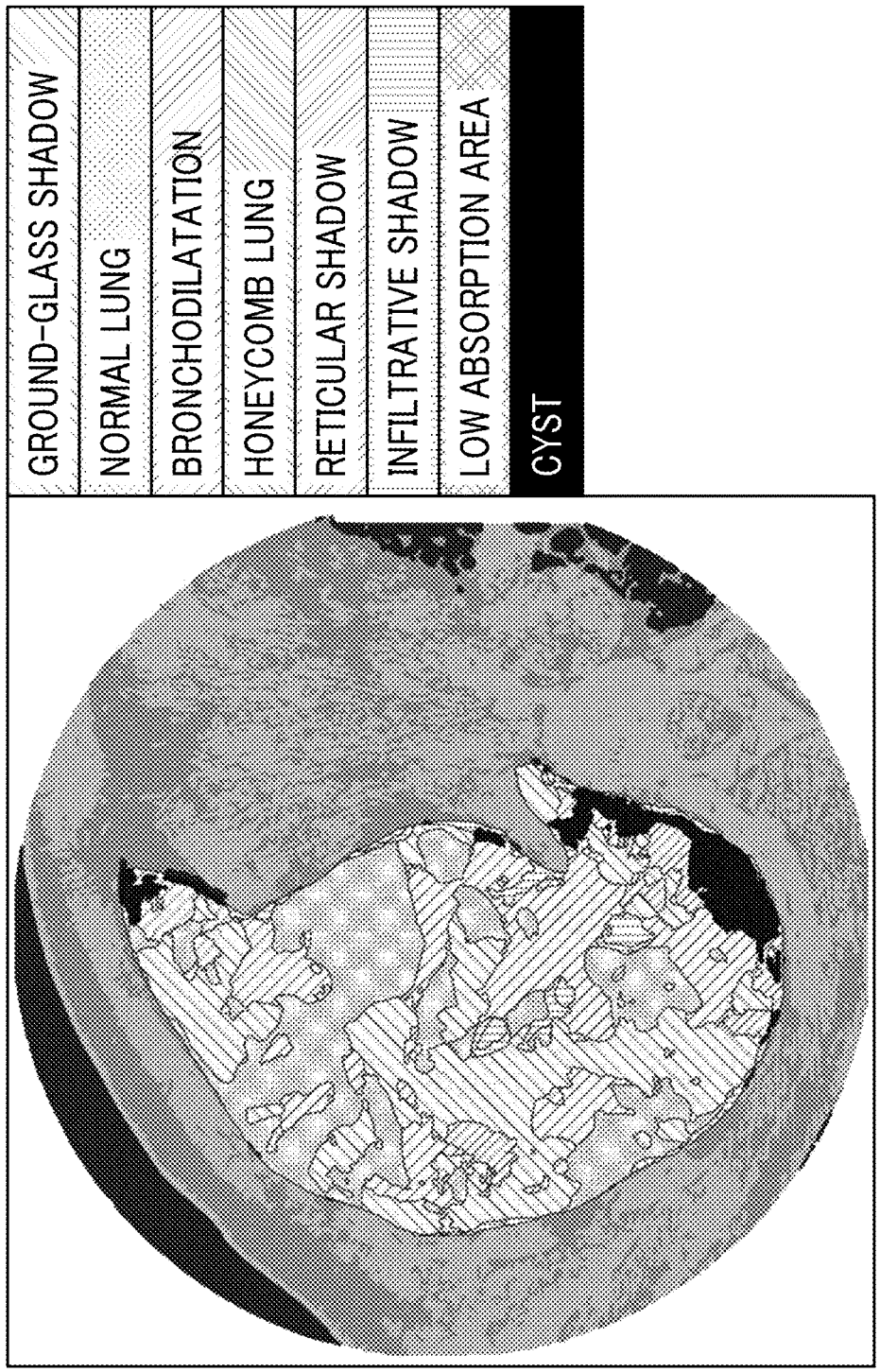

SIMILARITY DETERMINATION APPARATUS, SIMILARITY DETERMINATION METHOD, AND SIMILARITY DETERMINATION PROGRAM

CROSS REFERENCE TO RELATED APPLICATIONS

The present application is a Continuation of PCT International Application No. PCT/JP2019/041478 filed on Oct. 23, 2019, which claims priority under 35 U.S.C. § 119(a) to Japanese Patent Application No. 2018-221166 filed on Nov. 27, 2018. Each of the above applications is hereby expressly incorporated by reference, in its entirety, into the present application.

BACKGROUND

Technical Field

The present disclosure relates to a similarity determination apparatus, a similarity determination method, and a similarity determination program that determine a similarity between two medical images.

Related Art

In recent years, with the progress of medical apparatuses, such as a computed tomography (CT) apparatus and a magnetic resonance imaging (MRI) apparatus, high-resolution three-dimensional images with higher quality have been used for image diagnosis.

On the other hand, in the medical field, a similar case search apparatus has been known which searches for past cases similar to an examination image, such as a CT image to be examined, on the basis of the examination image (for example, see "Case-based lung image categorization and retrieval for interstitial lung diseases: clinical workflows, Adrien Depeursinge et al., Int J CARS (2012) 7:97-110, Published online: 1 Jun. 2011"). The literature of Depeursinge et al. discloses a method which classifies a case image of the lung into a plurality of regions indicating a plurality of types of tissues or lesions (hereinafter, it is assumed that tissues or lesions are generically referred to as findings), registers the plurality of regions in a case database, similarly classifies an examination image of the lung into a plurality of regions indicating a plurality of types of findings, and searches for a case image similar to the examination image on the basis of the classification result of the findings for the examination image.

In addition, as a method for calculating the similarity between images, a method has been proposed which sets a plurality of partial regions in at least one of a plurality of images, determines the similarity between each of the set partial regions and each corresponding region in other images, and weights and adds the determined similarities for each partial region using a weighting coefficient set for each partial region to calculate the overall region similarity (see JP2000-342558A). Further, a method has been proposed which divides a region of interest acquired from each cross section of a first image and a second image having a plurality of cross sections into a plurality of partial regions, calculates the feature amount of pixels included in the partial region for each cross section and each partial region of the first image and the second image, calculates the degree of coincidence between the feature amounts for the partial region of the first image and the partial region of the second image corresponding to the partial region of the first image in a combination of the positions of the cross sections of the first image and the second image, and specifies the positions of the corresponding cross sections of the first image and the second image on the basis of the comparison of evaluation values obtained by integrating the degree of coincidence over the plurality of partial regions (see JP2017-189384A).

However, interstitial pneumonia is known as a lung disease. A method has been proposed which analyzes a CT image of a patient with interstitial pneumonia to classify and quantify lesions indicating specific findings, such as a honeycomb lung, a reticular shadow, and a cyst, included in the CT image (see "Evaluation of computer-based computer tomography stratification against outcome models in connective tissue disease-related interstitial lung disease: a patient outcome study, Joseph Jacobi et al., BMC Medicine (2016) 14:190, DOI 10.1186/s12916-016-0739-7" and "Quantitative Evaluation of CT Images of Interstitial Pneumonia by Computer, Iwasawa Tae, Japanese Journal of Tomography, vol. 41, No. 2, August 2014"). The method which analyzes a CT image and classifies and quantifies lesions makes it possible to easily determine the degree of lung disease. In addition, different colors are assigned to the classified and quantified regions and the regions are displayed, which makes it possible to easily diagnose how much a specific symptom region is included in the image.

Further, it is necessary to detect a structure in a three-dimensional image in order to extract a structure, such as an organ of interest, from a three-dimensional image such as a CT image. Here, a deep learning method has been proposed in order to classify the pixels of interest in an image into a plurality of classes. Deep learning is a machine learning method using a multi-layer neural network constructed by hierarchically connecting a plurality of processing layers.

In deep learning, in each layer of the multi-layer neural network, arithmetic processing is performed for a plurality of different arithmetic result data items obtained by the previous layer for input data, that is, data of the extraction result of feature amounts. Then, in the subsequent processing layers, arithmetic processing is further performed for the obtained data of the feature amounts to improve the recognition rate of the feature amounts, and the input data can be classified into a plurality of classes.

It is considered that the deep learning method is applied to the above-mentioned three-dimensional image to classify each pixel of the three-dimensional image into a plurality of classes. For example, in a case in which a plurality of types of structures included in a three-dimensional image are classified, deep learning is performed for a neural network, using a three-dimensional image as an input, such that the pixel to be processed in the three-dimensional image is classified into any one of a plurality of types of structures. The use of the neural network subjected to the deep learning makes it possible to classify a pixel to be processed of the input three-dimensional image into any one of the plurality of types of structures.

The method disclosed in the literature of Depeursinge et al. can be used to search for a case image including a lesion similar to the lesion included in the lung in the examination image. On the other hand, the importance of a characteristic finding included in the examination image varies depending on the size of the finding. Further, the use of the methods described in JP2000-342558A and JP2017-189384A makes it possible to determine the similarity between images in consideration of the partial regions of the images or to specify the positions of the corresponding partial regions. On the other hand, in particular, in a case in which the search target is a three-dimensional image, it is important to search for case images similar to the examination image in consideration of the tomographic plane, which a doctor is paying attention to, in the examination image.

SUMMARY OF THE INVENTION

The present disclosure has been made in view of the above-mentioned problems, and an object of the present disclosure is to provide a technique that can appropriately determine a similarity between medical images according to the size of findings included in the medical images in consideration of a tomographic plane which a doctor is paying attention to.

According to the present disclosure, there is provided a similarity determination apparatus that determines a similarity between a first three-dimensional medical image and a second three-dimensional medical image. The similarity determination apparatus comprises: a display control unit that displays a tomographic image of a specific tomographic plane in the first medical image on a display unit; a finding classification unit that classifies each pixel of a partial region including at least the specific tomographic plane in the first medical image into at least one of a plurality of types of findings; a feature amount calculation unit that calculates a first feature amount for each finding classified in the partial region; a weighting coefficient setting unit that sets a weighting coefficient indicating a degree of weighting, which varies depending on a size of each finding, for each finding classified in the partial region; and a similarity derivation unit that performs a weighting operation for the first feature amount for each finding calculated in the partial region and a second feature amount for each finding calculated in advance in the second medical image on the basis of the weighting coefficient to derive the similarity between the first medical image and the second medical image.

Further, in the similarity determination apparatus according to the present disclosure, the similarity derivation unit may derive region similarities between the partial region and each of a plurality of small regions in the second medical image and may determine a representative similarity among the plurality of region similarities as the similarity between the first medical image and the second medical image.

Any similarity representing the plurality of region similarities can be used as the representative similarity. For example, a maximum similarity, an intermediate similarity, an average similarity, and a value obtained by adding a predetermined number of top similarities among the plurality of region similarities can be used.

Furthermore, in the similarity determination apparatus according to the present disclosure, the similarity derivation unit may increase a region similarity for a small region that is positionally closer to the partial region among the plurality of small regions and may determine the representative similarity.

Moreover, in the similarity determination apparatus according to the present disclosure, the second medical image may be divided into the plurality of small regions having overlapping regions.

In addition, in the similarity determination apparatus according to the present disclosure, the first medical image may be divided into a plurality of small regions in advance, the first feature amount may be calculated in advance in each of the plurality of small regions, and the weighting coefficient may be set in each of the plurality of small regions. The similarity derivation unit may use the small region including the specific tomographic plane as the partial region and may perform the weighting operation for the first feature amount for each finding calculated in advance in the partial region and the second feature amount for each finding calculated in advance in the second medical image on the basis of the weighting coefficient to derive the similarity between the first medical image and the second medical image.

Further, in the similarity determination apparatus according to the present disclosure, the finding classification unit may include a discriminator that has been subjected to machine learning so as to classify the plurality of types of findings and may classify each pixel of the partial region into the plurality of types of findings using the discriminator.

Furthermore, in the similarity determination apparatus according to the present disclosure, the finding classification unit may classify each pixel of the first medical image into at least one of the plurality of types of findings. The feature amount calculation unit may calculate a third feature amount for each finding classified in the first medical image. The weighting coefficient setting unit may set, as a first weighting coefficient, the weighting coefficient indicating the degree of weighting, which varies depending on the size of each finding, for each finding classified in the partial region and may set, as a second weighting coefficient, a weighting coefficient indicating a degree of weighting, which varies depending on the size of each finding, for each finding classified in the first medical image. The similarity derivation unit may perform the weighting operation for the first feature amount for each finding calculated in the partial region and the second feature amount for each finding calculated in advance in the second medical image on the basis of the first weighting coefficient to derive the similarity between the first medical image and the second medical image as a first similarity, may perform a weighting operation for the third feature amount for each finding calculated in the first medical image and a fourth feature amount for each finding calculated in advance in the second medical image on the basis of the second weighting coefficient to derive a similarity between the first medical image and the second medical image as a second similarity, and may derive a final similarity between the first medical image and the second medical image on the basis of the first similarity and the second similarity.

In addition, in the similarity determination apparatus according to the present disclosure, the similarity derivation unit may weight and add the first similarity and the second similarity to derive the final similarity.

Further, in the similarity determination apparatus according to the present disclosure, the similarity derivation unit may be capable of changing a weighting coefficient in a case in which the first similarity and the second similarity are weighted and added.

Moreover, the similarity determination apparatus according to the present disclosure may further comprise a search unit that searches for the second medical image similar to the first medical image as a similar medical image on the basis of similarities between the first medical image and a plurality of second medical images with reference to a case database in which the plurality of second medical images are registered and the second feature amounts for each of the plurality of second medical images are registered so as to be associated with the plurality of second medical images.

In addition, the similarity determination apparatus according to the present disclosure may further comprise a search unit that searches for the second medical image similar to the first medical image as a similar medical image on the basis of the final similarities between the first medical image and a plurality of second medical images with reference to a case database in which the plurality of second medical images are registered and the second and fourth feature amounts for each of the plurality of second medical images are registered so as to be associated with each of the plurality of second medical images.

Further, in the similarity determination apparatus according to the present disclosure, in a case in which the tomographic image of the specific tomographic plane is displayed for a predetermined time, the search unit may perform the search.

Furthermore, in the similarity determination apparatus according to the present disclosure, the display control unit may display a search result of the similar medical image on the display unit.

According to the present disclosure, there is provided a similarity determination method that determines a similarity between a first three-dimensional medical image and a second three-dimensional medical image. The similarity determination method comprises: displaying a tomographic image of a specific tomographic plane in the first medical image on a display unit; classifying each pixel of a partial region including at least the specific tomographic plane in the first medical image into at least one of a plurality of types of findings; calculating a first feature amount for each finding classified in the partial region; setting a weighting coefficient indicating a degree of weighting, which varies depending on a size of each finding, for each finding classified in the partial region; and performing a weighting operation for the first feature amount for each finding calculated in the partial region and a second feature amount for each finding calculated in advance in the second medical image on the basis of the weighting coefficient to derive the similarity between the first medical image and the second medical image.

In addition, a program that causes a computer to perform the similarity determination method according to the present disclosure may be provided.

Another similarity determination apparatus according to the present disclosure comprises a memory that stores commands to cause a computer to perform a process of determining a similarity between a first medical image and a second medical image and a processor configured to execute the stored commands. The processor performs a process of: displaying a tomographic image of a specific tomographic plane in the first medical image on a display unit; classifying each pixel of a partial region including at least the specific tomographic plane in the first medical image into at least one of a plurality of types of findings; calculating a first feature amount for each finding classified in the partial region; setting a weighting coefficient indicating a degree of weighting, which varies depending on a size of each finding, for each finding classified in the partial region; and performing a weighting operation for the first feature amount for each finding calculated in the partial region and a second feature amount for each finding calculated in advance in the second medical image on the basis of the weighting coefficient to derive the similarity between the first medical image and the second medical image.

According to the present disclosure, it is possible to appropriately determine the similarity between the first medical image and the second medical image according to the size of findings included in the medical images in consideration of the tomographic plane which the doctor is paying attention to.

BRIEF DESCRIPTION OF THE DRAWINGS

FIG. 6 is a diagram illustrating an evaluation value corresponding to the type of finding for a central pixel of a certain region of interest.

FIG. 7 is a diagram illustrating calculation results of the volumes of findings.

FIG. 19 is a diagram illustrating a mapping image to which colors corresponding to classifications are assigned.

DETAILED DESCRIPTION

Figure 1:
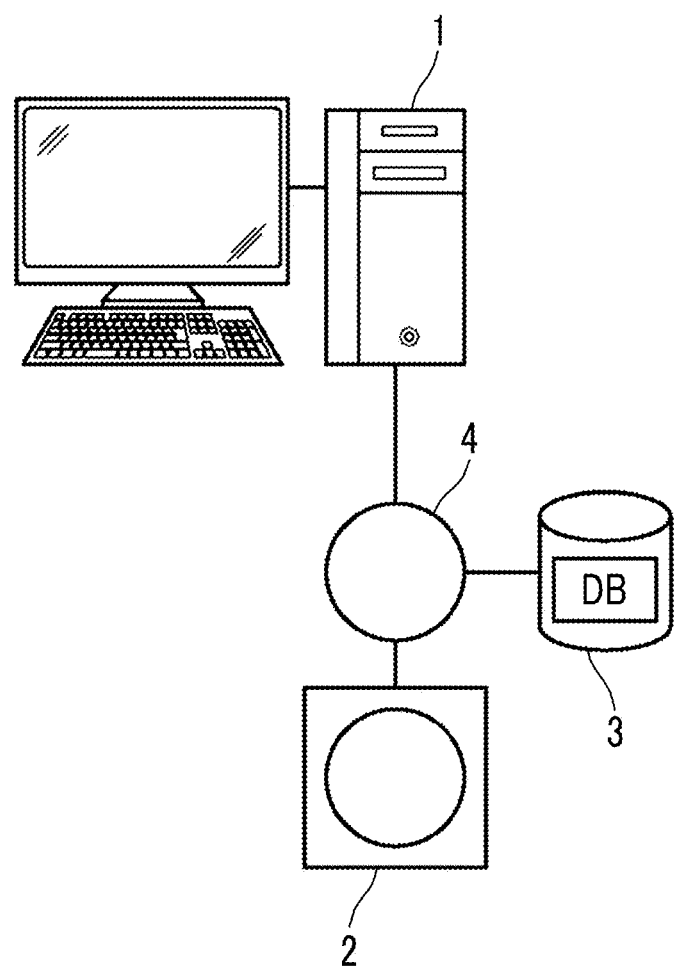
FIG. 1 is a hardware configuration diagram illustrating the outline of a diagnosis support system to which a similarity determination apparatus according to a first embodiment of the present disclosure is applied.

Hereinafter, embodiments of the present disclosure will be described with reference to the drawings. FIG. 1 is a hardware configuration diagram illustrating the outline of a diagnosis support system to which a similarity determination apparatus according to a first embodiment of the present disclosure is applied. As illustrated in FIG. 1, in the diagnosis support system, a similarity determination apparatus 1 according to this embodiment, a three-dimensional imaging apparatus 2, and an image storage server 3 are connected so as to communicate with each other through a network 4.

The three-dimensional imaging apparatus 2 is an apparatus that captures an image of a diagnosis target part of a subject to generate a three-dimensional image indicating the part and is, specifically, a CT apparatus, an MRI apparatus, a positron emission tomography (PET) apparatus, and the like. The three-dimensional image which consists of a plurality of slice images and has been generated by the three-dimensional imaging apparatus 2 is transmitted to the image storage server 3 and is then stored therein. In addition, in this embodiment, the diagnosis target part of a patient that is the subject is the lung, and the three-dimensional imaging apparatus 2 is a CT apparatus and generates a CT image of the chest including the lung of the subject as the three-dimensional image.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including the image data of the three-dimensional image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM). In this embodiment, it is assumed that the image storage server 3 stores three-dimensional images to be examined (hereinafter, referred to as examination images) and a case database DB having case images registered therein. The case database DB will be described below. In addition, in this embodiment, the examination image is a three-dimensional image consisting of one or more slice images (hereinafter, referred to as examination slice images). The case image is also a three-dimensional image consisting of one or more slice images (hereinafter, referred to as case slice images). Further, the examination image corresponds to a first medical image and the case image corresponds to a second medical image.

The similarity determination apparatus 1 is configured by installing a similarity determination program according to the present disclosure in one computer. The computer may be a workstation or a personal computer that is directly operated by a doctor who makes a diagnosis or may be a server computer that is connected to them through the network. The similarity determination program is recorded on a recording medium, such as a digital versatile disc (DVD) or a compact disc read only memory (CD-ROM), is distributed, and is installed in the computer from the recording medium. Alternatively, the similarity determination program is stored in a storage device of a server computer connected to the network, or is stored in a network storage so as to be accessed from the outside, is downloaded to the computer used by the doctor on request, and is then installed in the computer.

Figure 2:
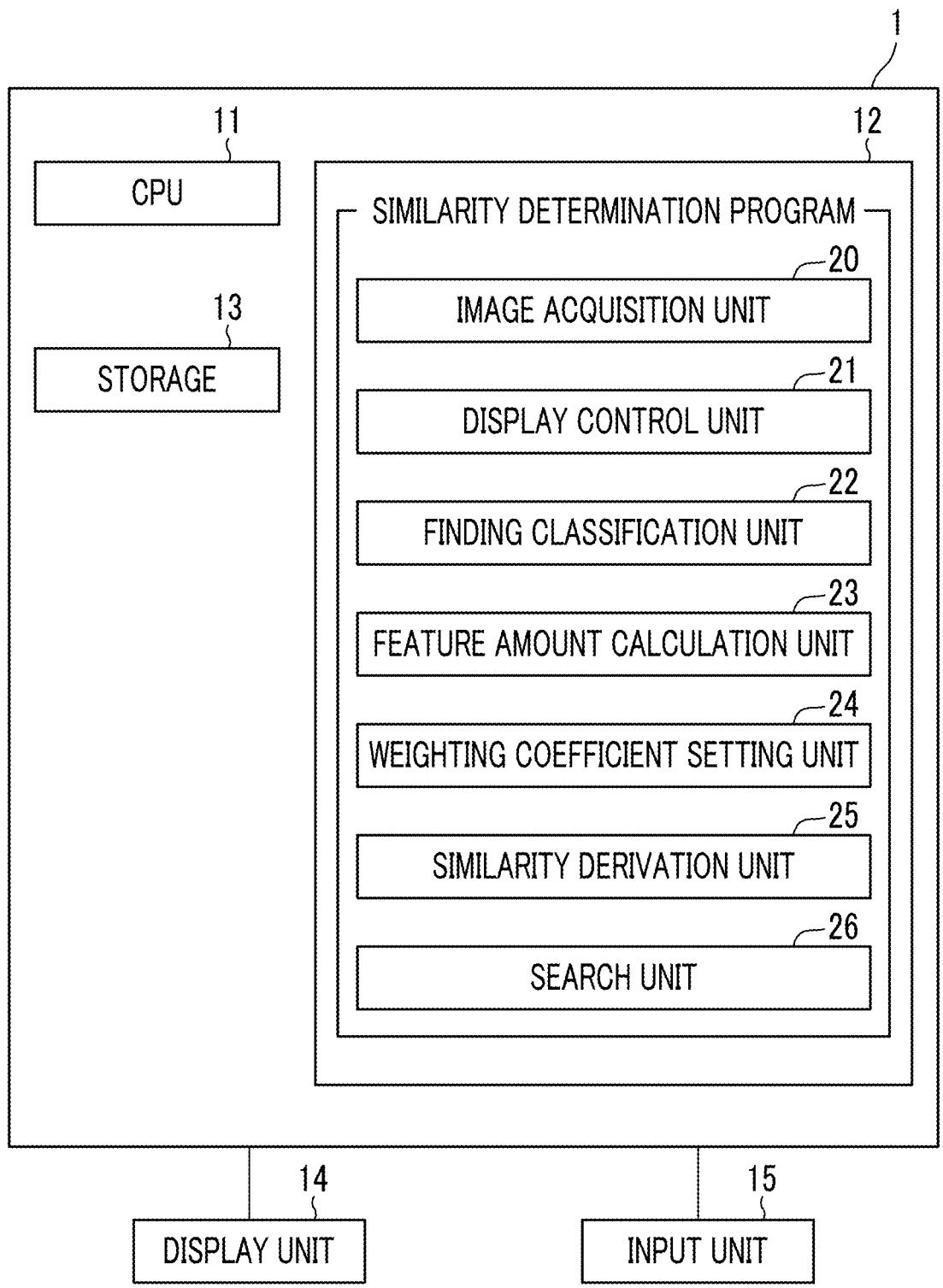
FIG. 2 is a block diagram schematically illustrating the configuration of the similarity determination apparatus according to the first embodiment.

FIG. 2 is a diagram schematically illustrating the configuration of the similarity determination apparatus according to the first embodiment of the present disclosure which is implemented by installing the similarity determination program in a computer. As illustrated in FIG. 2, the similarity determination apparatus 1 has the configuration of a standard workstation and comprises a central processing unit (CPU) 11, a memory 12, and a storage 13. In addition, a display unit 14 consisting of, for example, a liquid crystal display and an input unit 15 consisting of, for example, a keyboard and a mouse are connected to the similarity determination apparatus 1.

The storage 13 consists of, for example, a hard disk drive and a solid state drive (SSD). The storage 13 stores various kinds of information which include the examination image of the subject and information required for processes and are acquired from the image storage server 3 through the network 4.

Further, the memory 12 stores the similarity determination program. The similarity determination program defines the following processes as the processes performed by the CPU 11: an image acquisition process that acquires an examination image to be examined; a first display control process that displays an examination slice image of a specific tomographic plane in the examination image on the display unit 14; a finding classification process that classifies each pixel of a partial region including at least the specific tomographic plane in the examination image into at least one of a plurality of types of findings; a feature amount calculation process that calculates a first feature amount for each finding classified in the partial region of the examination image; a weighting coefficient setting process that sets a weighting coefficient indicating the degree of weighting, which varies depending on the size of each finding, for each finding classified in the partial region of the examination image; a similarity derivation process that performs a weighting operation for a first feature amount for each finding calculated in the partial region of the examination image and a second feature amount for each finding calculated in advance in a case image on the basis of the weighting coefficient to derive a similarity between the examination image and the case image; a search process that searches for a case image similar to the examination image on the basis of the derived similarity; and a second display control process that displays the search results on the display unit 14.

Then, the CPU 11 performs these processes according to the program such that the computer functions as an image acquisition unit 20, a display control unit 21, a finding classification unit 22, a feature amount calculation unit 23, a weighting coefficient setting unit 24, a similarity derivation unit 25, and a search unit 26.

The image acquisition unit 20 acquires an examination image V0 of the subject to be examined. Further, in a case in which the examination image V0 has already been stored in the storage 13, the image acquisition unit 20 may acquire the examination image V0 from the storage 13.

Figure 3:
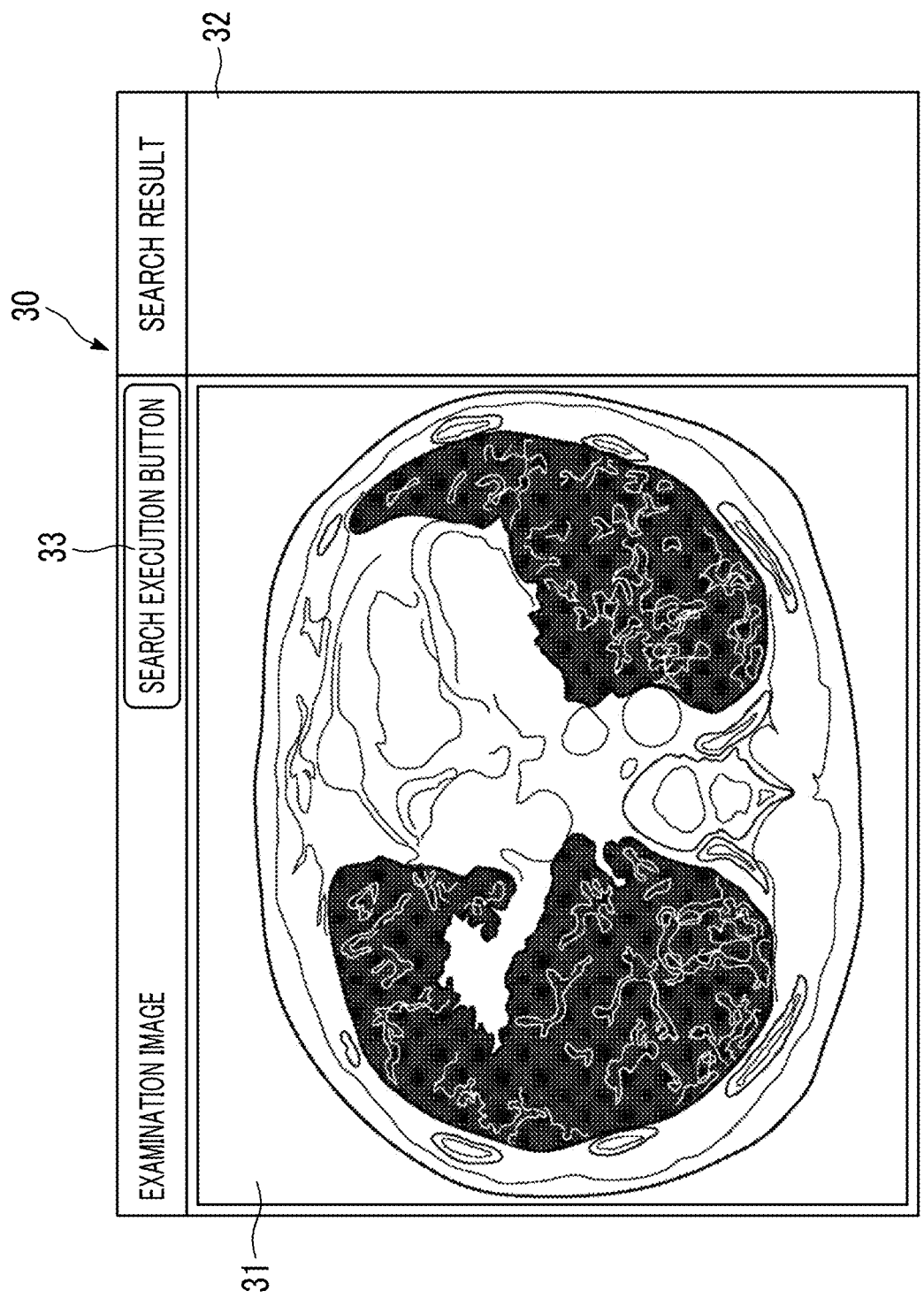
FIG. 3 is a diagram illustrating an examination slice image display screen.

The display control unit 21 performs the first display control process to display an examination slice image of a specific tomographic plane in the examination image on the display unit 14. FIG. 3 is a diagram illustrating an examination slice image display screen. As illustrated in FIG. 3, a display screen 30 has an examination slice image display region 31 and a search result display region 32. In addition, a search execution button 33 is displayed above the examination slice image display region 31. In the examination slice image display region 31, the examination slice image included in the examination image is displayed so as to be switchable in response to an instruction from the input unit 15. Further, an examination slice image of an axial cross section is displayed in FIG. 3. However, the present disclosure is not limited thereto, and an examination slice image of a sagittal cross section or a coronal cross section may be displayed. The doctor sequentially switches the examination slice image such that the examination slice image of a specific tomographic plane including a lesion can be displayed in the examination slice image display region 31. In addition, the search result display region 32 and the search execution button 33 will be described below.

The finding classification unit 22 classifies each pixel of a partial region including the tomographic plane of the displayed examination slice image in a lung region included in the examination image V0 into at least one of a plurality of types of findings. Specifically, the finding classification unit 22 calculates a plurality of evaluation values indicating the possibility that each pixel of the partial region including the tomographic plane of the displayed examination slice image in the lung region included in the examination image V0 will be each of a plurality of types of tissues or lesions (for example, findings) and classifies each pixel of the partial region of the examination image V0 into at least one of the plurality of types of findings on the basis of the plurality of evaluation values. In this embodiment, it is assumed that the finding classification unit 22 classifies each pixel of the partial region into one finding.

First, the finding classification unit 22 extracts the lung region which is a target region from the examination image V0 for classification. Any method, such as a method that creates a histogram of the signal value of each pixel of the examination image V0 and performs threshold processing for the lung to extract the lung region or a region growing method based on a seed point indicating the lung, can be used as a method of extracting the lung region. In addition, a discriminator which has been subjected to machine learning so as to extract the lung region may be used.

Figure 4:
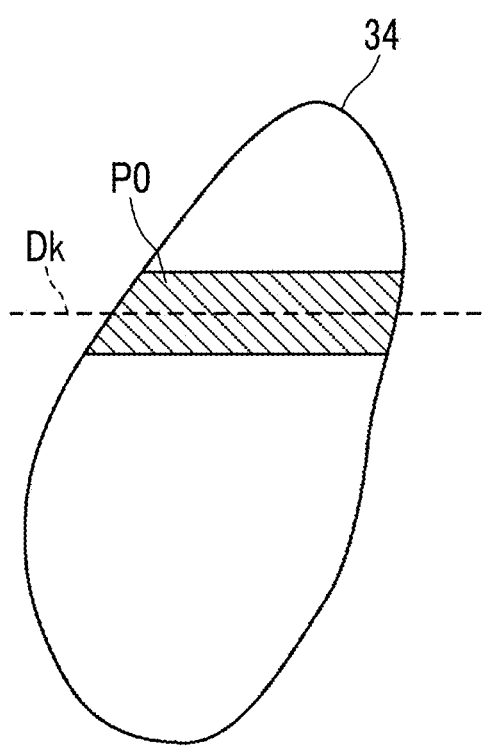
FIG. 4 is a diagram illustrating a partial region.

Hereinafter, the partial region will be described. FIG. 4 is a diagram illustrating a partial region. In addition, FIG. 4 is a diagram illustrating a lung region 34 of one lung included in the examination image as viewed from a direction orthogonal to the axial axis. In FIG. 4, a tomographic plane Dk of the examination slice image displayed on the display unit 14 is represented by a dashed line. The finding classification unit 22 sets, as a partial region P0, a region which has the tomographic plane Dk at the position of the center of gravity and is represented by a dashed line that divides the lung region into a predetermined number of equal parts by volume in the lung region 34 included in the examination image V0. Here, assuming that the predetermined number is 8, the volume of the partial region P0 is ⅛ of the volume of the lung region 34. Further, in this embodiment, the lung region is divided into eight equal parts. However, the present disclosure is not limited thereto, and the lung region may be divided into any number of parts such as four equal parts or six equal parts.

The finding classification unit 22 according to this embodiment includes a discriminator which consists of a multi-layer neural network generated by deep learning that is one kind of machine learning and specifies the type of finding, to which each pixel of the partial region P0 belongs, using the discriminator. In addition, a machine learning method is not limited to deep learning and other methods including a support vector machine may be used.

In each layer of the multi-layer neural network, arithmetic processing is performed for data of a plurality of different feature amounts obtained by the previous layer, using various kernels. Then, in the subsequent layers, arithmetic processing can be further performed for the data of the feature amounts obtained by the arithmetic processing to improve the recognition rate of the feature amounts and the input data can be classified into a plurality of classes.

Further, in this embodiment, the multi-layer neural network receives each pixel of the partial region P0 as an input and outputs the classification result of the lung region into a plurality of types of findings. However, the multi-layer neural network may be configured such that it receives each of a plurality of examination slice images constituting the partial region P0 as an input and outputs the classification result of the lung region into a plurality of types of findings.

Figure 5:
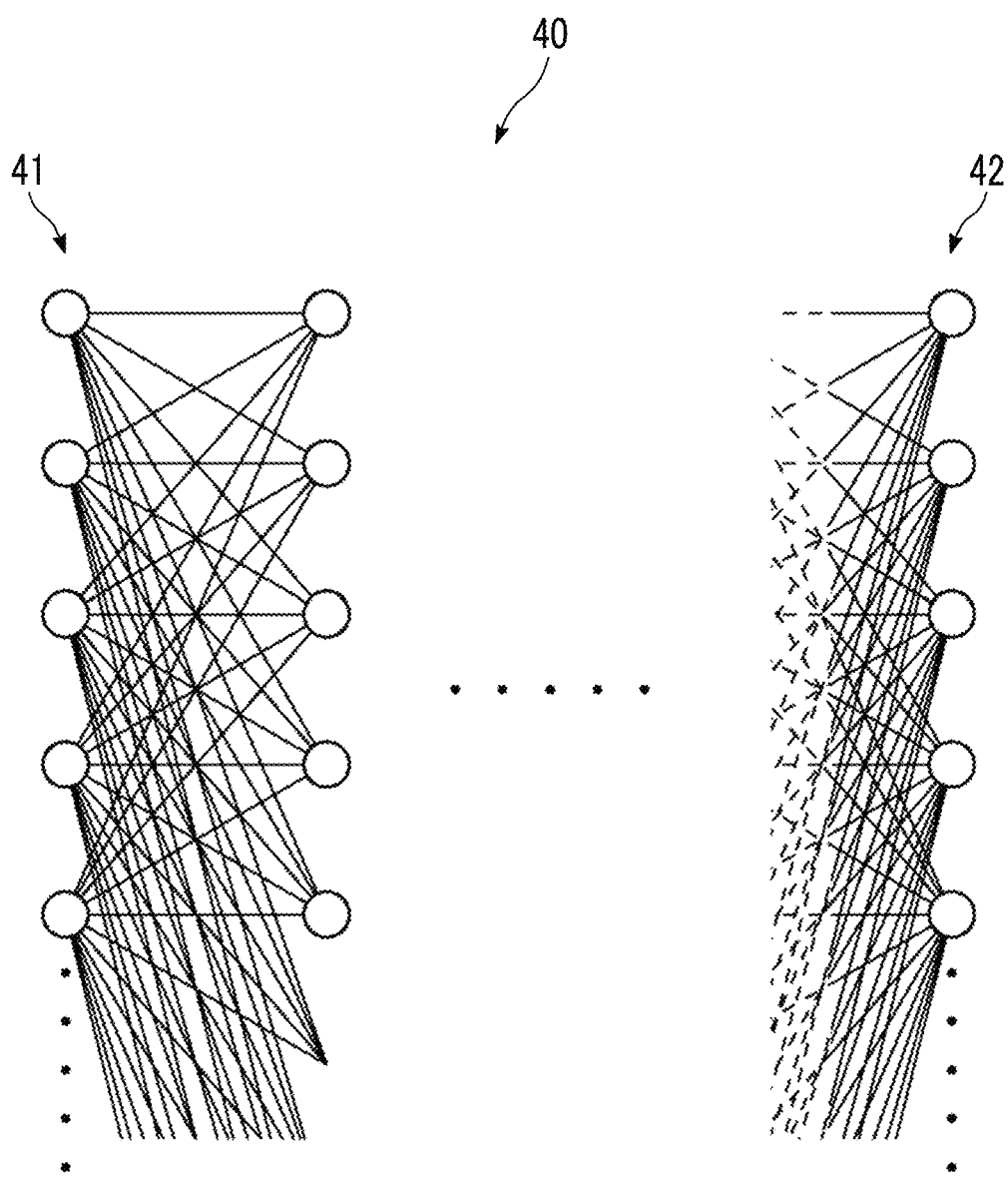
FIG. 5 is a diagram illustrating an example of a multi-layer neural network.

FIG. 5 is a diagram illustrating an example of the multi-layer neural network. As illustrated in FIG. 5, a multi-layer neural network 40 consists of a plurality of layers including an input layer 41 and an output layer 42. In this embodiment, learning is performed such that the partial region P0 of the lung region included in the examination image V0 is classified into a plurality of findings, such as an infiltrative shadow, a mass shadow, a ground-glass shadow, a centrilobular nodular shadow, a non-centrilobular nodular shadow, a reticular shadow, a linear shadow, interlobular septal thickening, a honeycomb lung, a cyst, a low absorption area (emphysema), emphysema tendency, a cavity, pleural thickening, pleural effusion, bronchodilatation, traction bronchiectasis, an artery, a normal lung, a chest wall, and mediastinum. In addition, the types of findings are not limited thereto and may be more or less than these findings.

In this embodiment, the multi-layer neural network 40 learns these findings using a large amount of training data such as millions of training data items. In the learning, a region of interest with a predetermined size (for example, 1.5 cm×1.5 cm) is cut out from a tomographic image in which the types of findings have been known. Then, the region of interest is used as the training data. Then, the training data is input to the multi-layer neural network 40 and the result of a finding type classification process (hereinafter, referred to as a classification result) is output from the multi-layer neural network 40. Then, the output result is compared with the training data, and the weight of the connection between the layers of units (represented by circles in FIG. 3) included in each layer of the multi-layer neural network 40 is corrected from the output side to the input side according to whether the answer is correct or incorrect. The correction of the weight of the connection is repeated using a large amount of training data a predetermined number of times or until the accuracy rate of the output classification result reaches 100%, and the learning ends.

Further, in a case in which the input image is the examination slice image, in the learning of the multi-layer neural network 40, a two-dimensional region normalized to a predetermined size (for example, 1.5 cm×1.5 cm) is cut out from a slice image forming a three-dimensional image in which a lesion has been known, and the image of the cut-out two-dimensional region is used as the training data.

In a case in which the finding classification process is performed, the finding classification unit 22 sequentially cuts out the region of interest having the same size as the training data from the partial region P0 and inputs the region of interest to the discriminator consisting of the multi-layer neural network 40. Then, for a central pixel of the cut-out region of interest, an evaluation value corresponding to each classification of the findings is output. In addition, the evaluation value corresponding to each classification is an evaluation value indicating the possibility that the central pixel will belong to each classification. As the evaluation value becomes larger, the possibility that the central pixel will belong to the classification becomes higher.

FIG. 6 is a diagram illustrating an evaluation value corresponding to the type of finding for a central pixel of a certain region of interest. Further, in FIG. 6, evaluation values for some findings are illustrated for simplicity of description. In this embodiment, the discriminator classifies the central pixel of the region of interest into a finding with the maximum evaluation value among a plurality of findings. For example, in a case in which the evaluation values illustrated in FIG. 6 are acquired, the central pixel of the region of interest has the highest possibility of being the reticular shadow and has the second highest possibility of being the ground-glass shadow. On the contrary, there is almost no possibility that the central pixel will be the normal lung or the low absorption area. Therefore, in a case in which the evaluation values as illustrated in FIG. 6 are acquired, the central pixel of the region of interest is classified into the reticular shadow having a maximum evaluation value of 8.5 by the finding classification process. In this way, all of the pixels of the lung region included in the partial region P0 of the examination image V0 are classified into any of the plurality of types of findings.

The finding classification unit 22 sequentially cuts out the same voxel region as the training data from the partial region P0 and sequentially inputs the cut-out voxel region to the discriminator consisting of the multi-layer neural network 40 which has been trained as described above. Then, for the central pixel of the cut-out region, a plurality of evaluation values for each of a plurality of types of lesion regions are output. The finding classification unit 22 classifies the central pixel of the region input to the multi-layer neural network 40 into a finding with the maximum evaluation value among the plurality of evaluation values and generates the classification result of the findings. Therefore, all of the pixels in the partial region P0 are classified into any of the plurality of types of findings.

The feature amount calculation unit 23 calculates a feature amount for each of the findings classified in the partial region P0. Specifically, the feature amount calculation unit 23 calculates, as the feature amount, at least one of the size of a region for each finding, average density for each finding, the variance of density for each finding, the number of regions for each finding, or the average size of the region for each finding. In addition, it is assumed that the feature amount calculated for the partial region P0 is referred to as a first feature amount. Further, for example, the size of the region for each finding, the number of regions for each finding, and the average size of the region for each finding are size feature amounts. The volume of the region for each finding can be used as the size of the region for each finding. The first feature amount is normalized to a value that is equal to or greater than 0 and equal to or less than 1.

The weighting coefficient setting unit 24 sets a weighting coefficient indicating the degree of weighting, which varies depending on the size of each finding, for each finding into which each pixel of the partial region P0 of the examination image V0 has been classified. The weighting coefficient is used for a weighting operation that is performed for the first feature amount for each finding calculated in the partial region P0 and the second feature amount for each finding calculated in advance prior to the similarity derivation process which will be described below in the case image which will be described below in the similarity derivation process.

Here, medical images have various features. Therefore, in a case in which the feature amounts are not appropriately weighted considering the importance of the feature amounts from the viewpoint of the medical images, the magnitude of the difference between the feature amounts does not correspond to the magnitude of the difference between the medical images, and the similarity deviates from the medical sense. Therefore, in a case in which the feature amounts are not appropriately weighted, in the search of a case image similar to the examination image V0, the search results are likely to be arranged in the order of inappropriate similarities.

Here, in a case in which the same findings having almost the same size are present in the examination image V0 and the case image, two images are medically similar to each other. Further, as a finding region becomes larger, the finding becomes more important in diagnosis. Therefore, the size of the finding is extremely important in determining the similarity between the images.

The findings include important findings, such as punctate shadows, that indicate the features of the initial state of a disease even in a case in which they have a small size.

Further, in a case in which lung emphysema progresses due to aging, a slightly low absorption state occurs in the lung. The finding of low absorption is less important because it is more common in older patients. The low absorption findings in elderly persons are not very important even though they have a large size.

Therefore, in a case in which the finding of the punctate shadow and the low absorption finding in an elderly person are equally determined, a subtle difference in the low absorption area of a large region is larger than a difference in the punctate shadow. As a result, the similarity between the punctate shadows is buried in the similarity between the low absorption areas, and it is difficult to search for a case image including a case of the punctate shadow that is medically important.

Therefore, in this embodiment, the weighting coefficient setting unit 24 sets the weighting coefficient indicating the degree of weighting, which varies depending on the size of each finding, for each of a plurality of findings. The size feature amount included in the first feature amount calculated by the feature amount calculation unit 23 can be used as the size of the finding. Specifically, the volume of the finding can be used. Here, the volume of the finding can be calculated by multiplying the number of pixels of each finding included in the partial region P0 of the three-dimensional examination image V0 by the volume per voxel in the examination image V0. FIG. 7 illustrates the calculation results of the volume of the findings. In FIG. 7, the unit of volume is cubic millimeters. The size of the lung varies depending on the patient. Therefore, it is preferable to use, as the size of the finding, finding occupancy (=the volume of the finding/the volume of the lung) obtained by normalizing the volume of the finding with the volume of the partial region P0. In this embodiment, it is assumed that finding occupancy is used as the size of the finding. In addition, the finding occupancy may be included as the size feature amount in the first feature amount. In this case, the feature amount calculation unit 23 may calculate the finding occupancy.

For each finding of the partial region P0 of the examination image V0, the weighting coefficient setting unit 24 sets a weighting coefficient Wi for each finding, using the following Expression (1). Further, in Expression (1), i is the type of finding, and fi is a function that has the finding occupancy Pvi of each finding in the partial region P0 of the examination image V0 as a parameter.

$$Wi = fi(Pvi) \quad (1)$$

Here, as illustrated in FIG. 7, the number of digits in the value of the volume is different between a finding with a large size and a finding with a small size. Therefore, it is preferable to reduce the dimensions, for example, by converting the finding occupancy, which is three-dimensional information, into two-dimensional finding occupancy using the function fi. In this case, the difference in the size of the finding is matched with the sense of the doctor. For this reason, as described above, it is preferable to nonlinearly convert a finding which has a small size, but is important using the function fi in order to increase the importance of the finding. Therefore, in this embodiment, the function fi is set as represented by the following Expression (2).

$$fi = a \cdot (b \cdot X + (1-b) \cdot X^c) \quad (2)$$

Further, in Expression (2), a is a constant that determines a difference in the overall importance of each finding. c is a constant that has a value of 1 or less and determines the effect of emphasizing a finding with a small size. b is a constant that determines the degree of the effect by the constant c. In addition, $X=(Pvi)^{2/3}$ is established. The finding occupancy Pvi is multiplied by ⅔ to be converted from a three-dimensional value to a two-dimensional value.

The weighting coefficient setting unit 24 sets the function represented by Expression (2) for each finding and applies the function to Expression (1) to set the weighting coefficient Wi for each of the plurality of types of findings.

Here, in organs, such as the lungs, there are lesions that spread diffusely and local lesions, such as lesions that are present only in a certain part of the organ. For the diffuse lesions, a desired case image can be searched by dividing a region as a similarity derivation target into a plurality of regions and deriving a similarity for each region. However, in the case of the local lesions, it is difficult to accurately derive the similarity due to a slight difference in the position of the boundary between the regions where the region is divided. As a result, it is difficult to search for a desired case image. In addition, in many cases, for diseases, the similarity between the features of the lesions is more important than the similarity between the positions of the lesions. In particular, in the case of a small lesion, as the size of the region to be divided becomes larger, the occupancy of the lesion in the region becomes lower. Therefore, it is difficult to accurately derive the similarity and to search for a desired case image.

Therefore, in this embodiment, the similarity with the case image and only the partial region P0 including the tomographic plane of the examination slice image displayed for the examination image V0 is derived. In addition, the similarity derivation unit 25 derives the similarities between the examination image V0 and all of the case images registered in the case database DB. Here, a plurality of case images, each of which consists of one or more case slice images, are registered in the case database DB. Specifically, a file name, evaluation values for a plurality of findings in each pixel, and feature amounts for each finding are registered for each of the plurality of case images. The feature amount registered in the case database DB for the case image is referred to as a second feature amount. Similarly to the first feature amount, the second feature amount is normalized to a value that is equal to or greater than 0 and equal to or less than 1.

Figure 8:
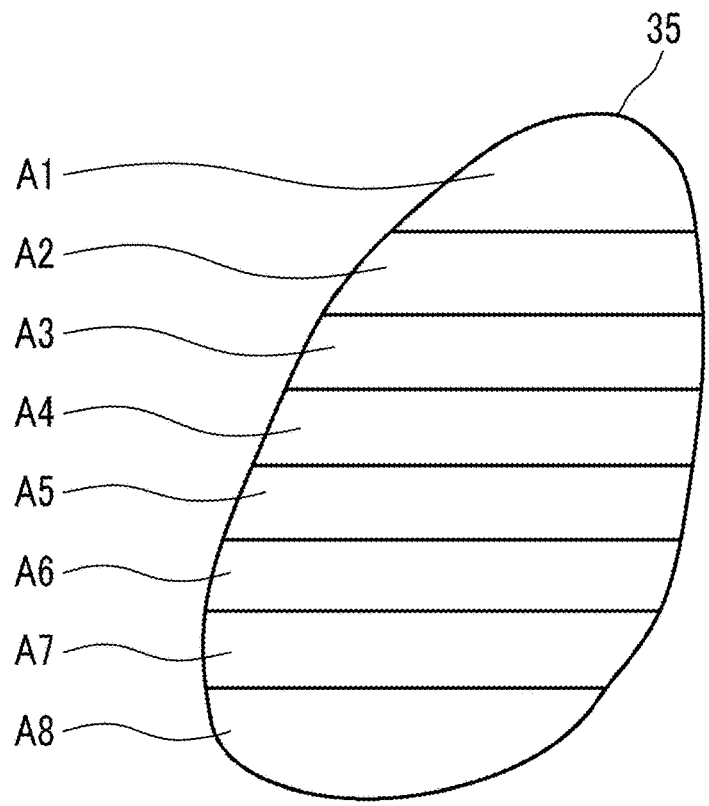
FIG. 8 is a diagram illustrating the division of a lung region of a case image into small regions.

Further, the lung region in the case image registered in the case database DB is divided into eight small regions A1 to A8 as illustrated in FIG. 8. Therefore, the similarity derivation unit 25 derives similarities (hereinafter, referred to as region similarities) S1 to S8 between the partial region P0 of the examination image V0 and the eight small regions A1 to A8 of the case image. Then, the maximum similarity among the derived eight region similarities S1 to S8 is defined as the similarity between the examination image V0 and the case image.

Further, in a case in which evaluation values for a plurality of findings in each pixel and feature amounts for each finding are acquired for the partial region P0 of the examination image V0, the examination image V0 is registered as a new case image in the case database DB. In this case, the lung region in the examination image V0 is divided into eight equal parts, and the evaluation value and the first feature amount in each of the eight small regions are registered as the evaluation value and the second feature amount of the new case image in the case database DB, respectively.

Hereinafter, the derivation of the similarity will be described. The similarity derivation unit 25 performs a weighting operation for the first feature amount for each finding calculated in the partial region P0 of the examination image V0 and the second feature amount for each finding calculated in advance in each of the small regions A1 to A8 of the case image on the basis of the weighting coefficient Wi set by the weighting coefficient setting unit 24 to derive the region similarities S1 to S8 between the partial region P0 of the examination image V0 and the small regions A1 to A8 of the case image.

Therefore, the similarity derivation unit 25 calculates, as a feature amount difference Ddi, a difference in distance between the first feature amount and the second feature amount of the case image for each finding, as represented by the following Expression (3). Further, in Expression (3), k indicates the type of feature amount, Tvk indicates the first feature amount for each type in the partial region P0 of the examination image V0, and Tck indicates the second feature amount for each type in the case image. Furthermore, the first feature amount and the second feature amount whose difference is calculated are the same type. In addition, in Expression (3), Σ indicates the calculation of the sum of $(Tvk-Tck)^2$ for all of the types of feature amounts. Further, since the first feature amount and the second feature amount are normalized to a value that is equal to or greater than 0 and equal to or less than 1, the feature amount difference Ddi is also a value that is equal to or greater than 0 and equal to or less than 1. Furthermore, in a case in which the first feature amount Tvk is equal to the second feature amount Tck, the feature amount difference Ddi is 0. Moreover, instead of the difference in the distance between the first feature amount and the second feature amount, for example, the absolute value of the difference between the first feature amount and the second feature amount may be used.

$$Ddi=\sqrt{(\Sigma(Tvk-Tck)^2)} \quad (3)$$

Then, the similarity derivation unit 25 calculates the region similarities Sj (j=1 to 8) between the partial region P0 of the examination image V0 and the small regions A1 to A8 of the case image with the following Expression (4) using the weighting coefficient Wi. That is, the similarity derivation unit 25 multiplies the feature amount difference Ddi by the weighting coefficient Wi for each finding and adds the multiplication results for all of the findings to calculate the region similarities S1 to S8. Further, in a case in which the region similarities S1 to S8 are calculated using Expression (4), the similarities between the partial region P0 of the examination image V0 and the small regions A1 to A8 of the case image become higher as the distance between the first feature amount and the second feature amount becomes shorter. Therefore, a negative sign is given to Expression (4) such that, as the similarities between the partial region P0 of the examination image V0 and the small regions A1 to A8 of the case image become higher, the values of the region similarities S1 to S8 become larger.

$$Sj=-\Sigma(Wi \times Ddi) \quad (4)$$

In contrast, in the calculation of the region similarities by Expression (4), in a case in which the same findings have the same size, the region similarities are 0. However, in a case in which the same lesions are compared with each other, the fact is that, as the size of the lesions becomes larger, the similarity between the lesions becomes higher. In a case in which the region similarities are calculated by Expression (4), there is no difference between a case in which findings having a relatively large size have the same feature amount and a case in which findings having a relatively small size have the same feature amount, and it is difficult to reflect the fact that, as the size of the lesions becomes larger, the similarity between the lesions becomes higher.

For this reason, for the same finding included in the partial region P0 of the examination image V0 and the small regions A1 to A8 of the case image, only the difference in size therebetween is not treated, and it is preferable that the similarity becomes higher as the sizes become more similar to each other. Therefore, in this embodiment, the similarity derivation unit 25 further calculates a difference Dsi between the sizes of the findings in the partial region P0 of the examination image V0 and the small regions A1 to A8 of the case image, using the following Expression (5). Further, in Expression (5), Pvi indicates the finding occupancy of a finding i in the partial region P0 of the examination image V0, and Pci indicates the finding occupancy of the finding i in the small regions A1 to A8 of the case image.

$$Dsi=1-|Pvi-Pci|/(Pvi+Pci) \quad (5)$$

Therefore, it is preferable that the similarity derivation unit 25 calculates region similarities Saj between the partial region P0 of the examination image V0 and the small regions A1 to A8 of the case image using the following Expression (6). Here, Ddi is a value that becomes smaller as the similarity between the feature amounts of the findings in the partial region P0 of the examination image V0 and the small regions A1 to A8 of the case image becomes higher, and Dsi is a value that becomes larger as the sizes of the findings in the partial region P0 of the examination image V0 and the small regions A1 to A8 of the case image become more similar to each other. Therefore, it is possible to calculate the region similarity that becomes higher as the partial region P0 of the examination image V0 becomes more similar to the small regions A1 to A8 of the case image using Expression (6), considering the sizes of the same findings.

$$Saj=\Sigma(Wi\times(Dsi-Ddi)) \quad (6)$$

Further, in a case in which the region similarities Saj are calculated by Expression (6), the maximum value of the region similarities Saj varies depending on the partial region P0 of the examination image V0. Therefore, it is preferable to normalize the region similarities Saj under the condition that the region similarities Saj between the partial region P0 of the examination image V0 and the small regions A1 to A8 of the case image are at their maximum, that is, the condition that there is no difference between the partial region P0 of the examination image V0 and the small regions A1 to A8 of the case image. Expression (7) is obtained by normalizing the region similarities Saj calculated by Expression (6) under the condition that the region similarities Saj between the partial region P0 of the examination image V0 and the small regions A1 to A8 of the case image are at their maximum. In Expression (7), Sbj indicates the normalized region similarity.

$$Sbj=Saj/\Sigma Wi=\Sigma(Wi\times(Dsi-Ddi))/\Sigma Wi \quad (7)$$

In addition, in a case in which the region similarities are calculated by Expression (4), it is also preferable to normalize the region similarities Sj. Expression (8) is obtained by normalizing Expression (4) under the condition that the region similarities Sj between the partial region P0 of the examination image V0 and the small regions A1 to A8 of the case image are at their maximum. In Expression (8), Scj indicates the normalized region similarity.

$$Scj=Sj/\Sigma Wi=\Sigma(Wi\times Dsi)/\Sigma Wi \quad (8)$$

Figure 9:
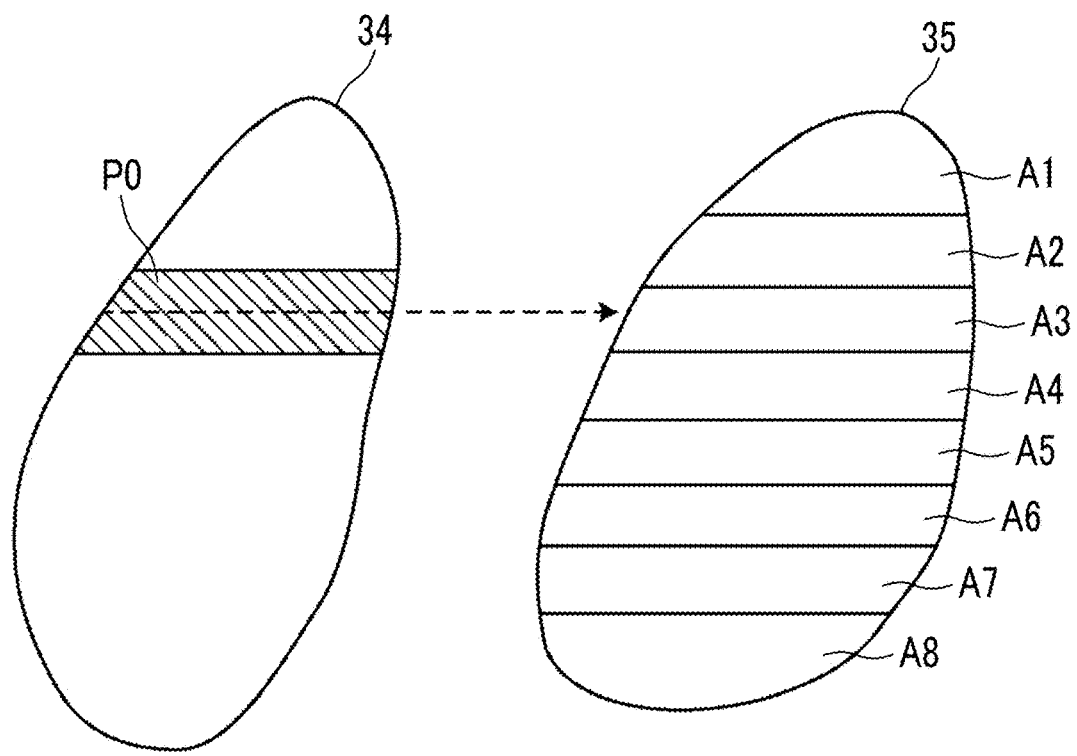
FIG. 9 is a diagram illustrating a correspondence between a partial region of an examination image and the small regions of the case image.

Further, in a case in which the region similarities are calculated, the lung region of the examination image V0 may be compared with the lung region of the case image, and the region similarity weighted by a larger value may be calculated for a small region that is positionally closer to the partial region P0 of the examination image V0 among the small regions A1 to A8 of the case image. For example, as illustrated in FIG. 9, in a lung region 34 of the examination image V0 and a lung region 35 of the case image, the partial region P0 of the examination image V0 and the small region A3 of the lung region 35 of the case image positionally correspond to each other. Therefore, in a case in which the calculated region similarity is Sbj, it is preferable to correct the region similarity Sbj using the following Expression (9) to derive a corrected region similarity Sdj. In Expression (9), k indicates a small region positionally corresponding to the partial region P0 (k=3 in the case illustrated in FIG. 9), and d indicates a constant that is equal to or less than a predetermined value of 1/the number of divisions. For example, in a case in which the number of divisions is 8, d=⅛.

$$Sdj=(1-d\times|k-j|)\times Sbj \quad (9)$$

By Expression (9), (1−d×|k−j|)=1 is established for the small region positionally corresponding to the partial region P0. Therefore, Sdj=Sbj is established. Further, as the position of the small region becomes farther from the partial region P0, d×|k−j| becomes larger. Therefore, the value of Sdj becomes smaller than the value of Sbj. Therefore, the similarity with the case image having a portion that is positionally closer to the partial region P0 of the examination image V0 becomes higher.

The similarity derivation unit 25 derives a representative region similarity among the region similarities between the partial region P0 of the examination image V0 and the small regions A1 to A8 of the case image derived as described above as a similarity Sf between the examination image V0 and the case image. In addition, the similarity Sf may be the maximum region similarity among the plurality of region similarities. However, the representative region similarity is not limited to the maximum region similarity. For example, the average value and the intermediate value of the plurality of region similarities and the addition value of a predetermined number of top region similarities may be used as long as the region similarity represents the plurality of region similarities.

Figure 10:
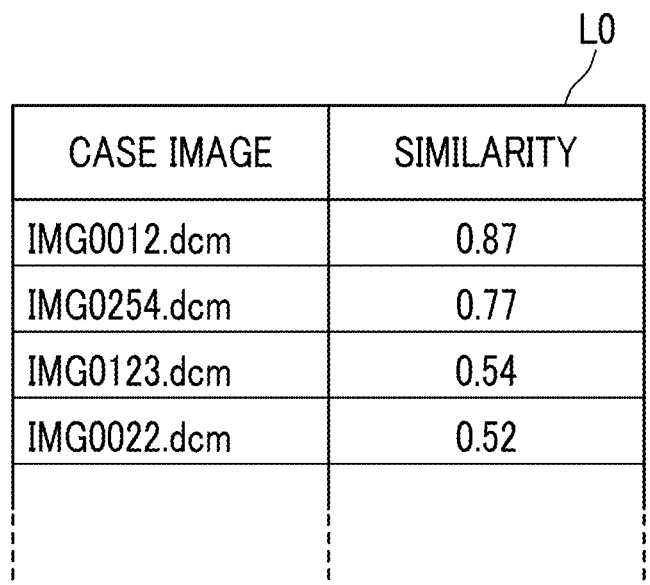
FIG. 10 is a diagram illustrating a search result list.

The search unit 26 performs a search process of searching for a case image similar to the examination image V0 as a similar case image from the case database DB on the basis of the similarity Sf. The search unit 26 searches for a case image similar to the examination image V0 as the similar case image on the basis of the similarities Sf between the examination image V0 and all of the case images registered in the case database DB. Specifically, the search unit 26 sorts the case images in descending order of the similarity Sf to create a search result list. FIG. 10 is a diagram illustrating the search result list. As illustrated in FIG. 10, the case images registered in the case database DB are sorted in descending order of the similarity Sf in a search result list L0. Then, the search unit 26 extracts a predetermined number of top case images sorted in the search result list L0 as the similar case images from the case database DB. In addition, the similar case image corresponds to a similar medical image.

Figure 11:
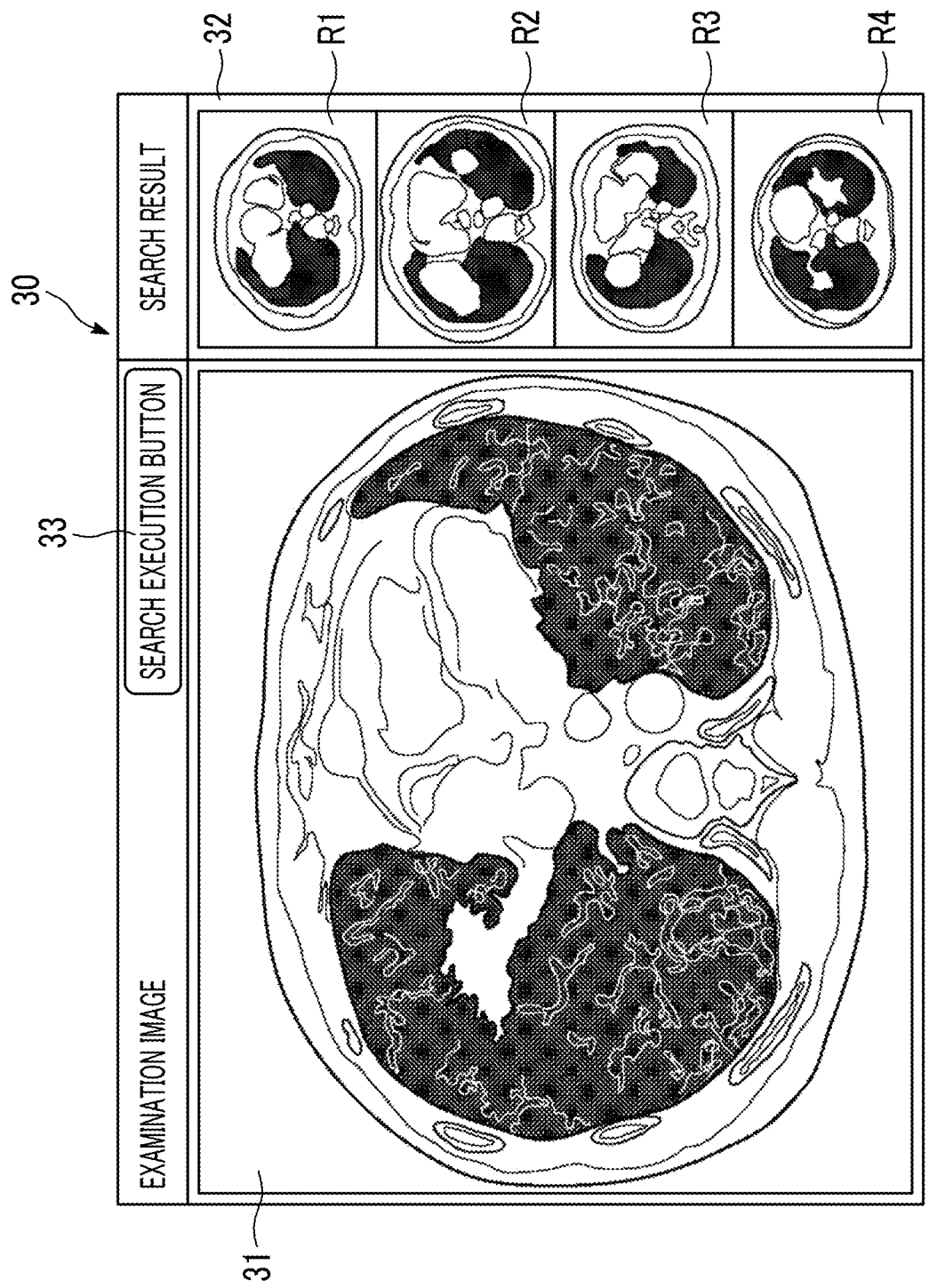
FIG. 11 is a diagram illustrating search results.

The display control unit 21 performs a second display control process to display the search results by the search unit 26 on the display unit 14. FIG. 11 is a diagram illustrating the search results. As illustrated in FIG. 11, similar case images R1 to R4 are displayed in the search result display region 32 of the display screen 30. In addition, here, four similar case images R1 to R4 are displayed. However, more similar case images may be displayed. In this case, the search result display region 32 can be scrolled to display similar case images that are not capable of being displayed in the search result display region 32.

Figure 12:
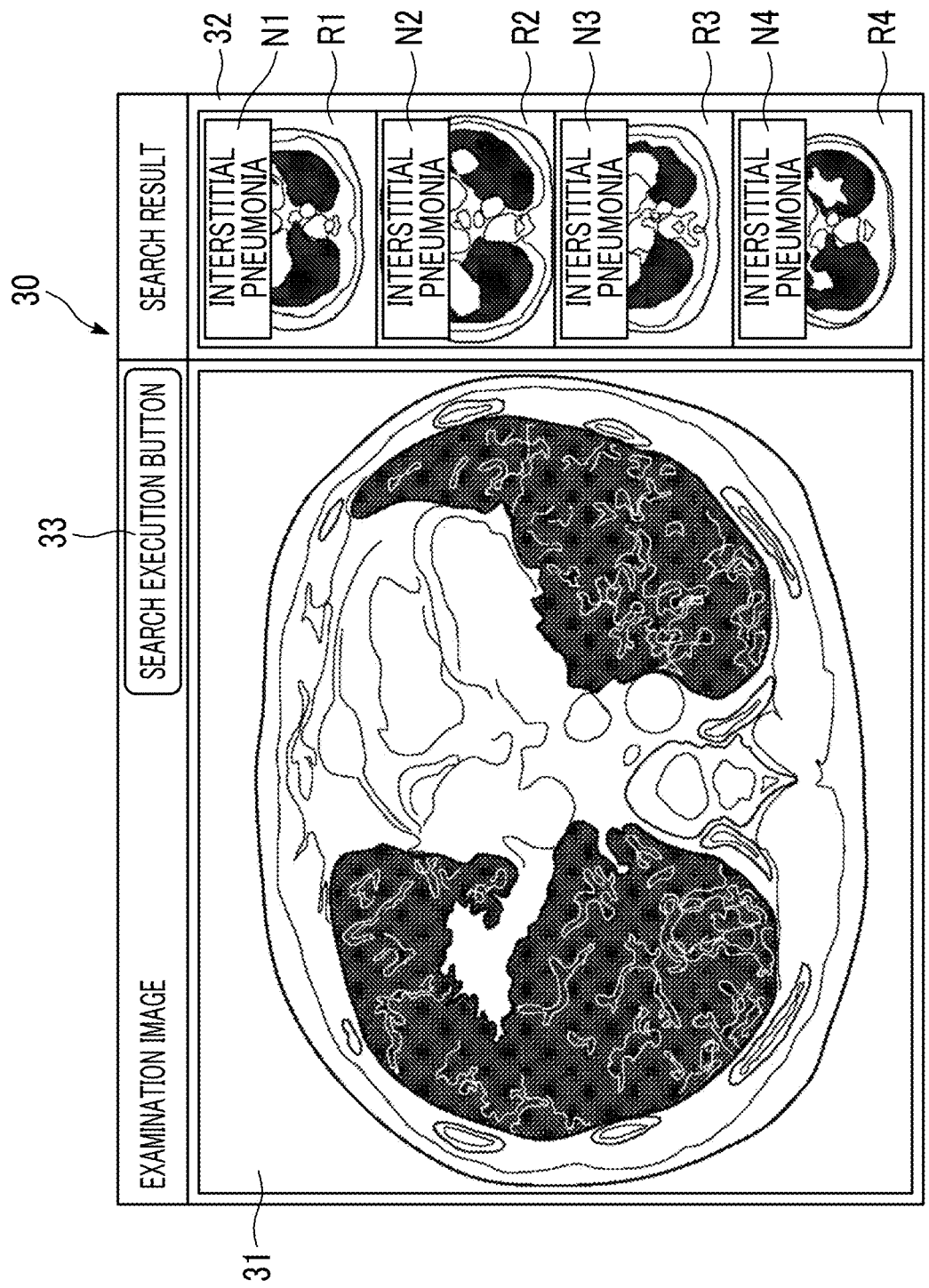
FIG. 12 is a diagram illustrating the search results in which case names are displayed.

Further, the similar case images R1 to R4 are the case slice images of the representative tomographic planes in the small regions having the maximum similarity with the partial region P0 of the examination image V0 in the case images. The representative tomographic plane may be, for example, a tomographic plane located at the center of gravity of the small region, but is not limited thereto. In addition, as illustrated in FIG. 12, disease names N1 to N4 may be displayed on the similar case images R1 to R4, respectively. In FIG. 12, the disease names N1 to N4 are "interstitial pneumonia". The disease names N1 to N4 may be acquired with reference to the case database DB.

Further, the finding classification unit 22, the feature amount calculation unit 23, the weighting coefficient setting unit 24, the similarity derivation unit 25, and the search unit 26 start the processes in response to the instruction of the search execution button 33 displayed on the display screen 30 illustrated in FIG. 3. However, the present disclosure is not limited thereto. For example, in a case in which the user inputs an instruction to switch and display the tomographic plane of the examination image V0, the examination slice image suspected to have a lesion is displayed in the examination slice image display region 31 of the display screen 30 so as to be observed. Therefore, in a case in which a predetermined time (for example, 0.5 seconds) has elapsed since the display of the examination slice image of a specific tomographic plane during the switching and display of the tomographic plane of the examination image V0, the finding classification unit 22, the feature amount calculation unit 23, the weighting coefficient setting unit 24, the similarity derivation unit 25, and the search unit 26 may start the processes and display the search results. In addition, in a case in which a predetermined time has elapsed since the display of the examination slice image of a specific tomographic plane, the finding classification unit 22, the feature amount calculation unit 23, the weighting coefficient setting unit 24, the similarity derivation unit 25, and the search unit 26 may start the processes to generate search results and display the search results immediately after the search execution button 33 is instructed.

Figure 13:
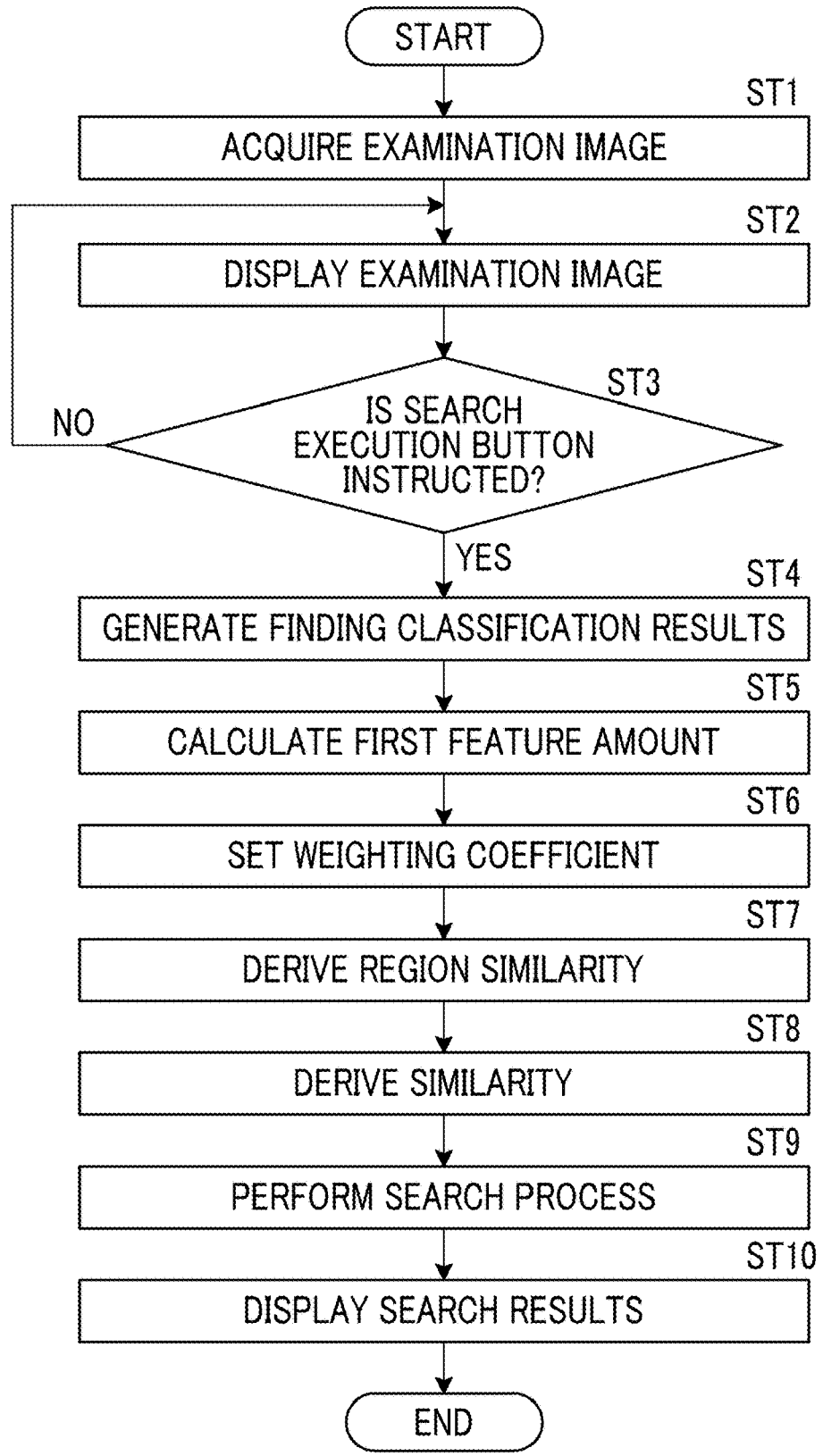
FIG. 13 is a flowchart illustrating a process performed in the first embodiment.

Next, a process performed in the first embodiment will be described. FIG. 13 is a flowchart illustrating the process performed in the first embodiment. First, the image acquisition unit 20 acquires the examination image V0 (Step ST1), and the display control unit 21 displays the examination image V0 on the display unit 14 (Step ST2). Then, in a case in which the search execution button 33 is instructed (Step ST3; YES), the finding classification unit 22 classifies the partial region P0 of the lung region included in the examination image V0 into a plurality of types of lesion regions indicating each of a plurality of types of findings and generates finding classification results (Step ST4). Then, the feature amount calculation unit 23 calculates the first feature amount for each of the findings classified in the partial region P0 of the examination image V0 (Step ST5). In addition, the weighting coefficient setting unit 24 sets the weighting coefficient Wi for each finding of the partial region P0 of the examination image V0 (Step ST6).

Then, the similarity derivation unit 25 performs a weighting operation for the first feature amount for each finding calculated in the partial region P0 of the examination image V0 and the second feature amount for each finding calculated in advance in the small regions A1 to A8 of the case image on the basis of the weighting coefficient Wi to derive the region similarities between the partial region P0 of the examination image V0 and the small regions A1 to A8 of the case image (Step ST7). Further, the similarity derivation unit 25 derives a representative similarity among the region similarities as the similarity between the examination image V0 and the case image (Step ST8). In addition, as described above, the similarity derivation unit 25 derives the similarities between the examination image V0 and all of the case images registered in the case database DB. Further, the search unit 26 performs the search process on the basis of the similarities (Step ST9), and the display control unit 21 displays the search results on the display unit 14 (Step ST10). Then, the process ends.

As described above, according to this embodiment, the examination slice image of a specific tomographic plane in the examination image V0 is displayed on the display unit 14, and each pixel of the partial region P0 including at least the specific tomographic plane in the examination image V0 is classified into at least one of a plurality of types of findings. Then, the first feature amount is calculated for each finding classified in the partial region P0, and the weighting coefficient indicating the degree of weighting, which varies depending on the size of each finding, is set for each finding classified in the partial region P0. Then, the weighting operation is performed for the first feature amount for each finding calculated in the partial region P0 and the second feature amount for each finding calculated in advance in the case image on the basis of the weighting coefficient to derive the similarity between the examination image V0 and the case image.

Here, the lesion occupancy of a small lesion that is present locally is low in the entire examination image V0, but is high in the partial region P0 of the examination image V0. Therefore, the use of the partial region P0 of the examination image V0 as in this embodiment makes it possible to calculate the feature amount for the small lesion without being affected by other lesions, other regions, and analysis errors. As a result, according to this embodiment, it is possible to appropriately determine the similarity between the examination image V0 and the case image according to the sizes of the findings included in the examination image V0 and the case image in consideration of the tomographic plane that the doctor is paying attention to.

Further, in this embodiment, the partial region P0 including the displayed tomographic image is set, and a case image similar to the examination image V0 is searched for. Therefore, it is possible to search for case images without marking a lesion or the like in the displayed tomographic image. As a result, it is possible to reduce the burden on the user's operation.

Next, a second embodiment of the present disclosure will be described. In addition, the configuration of a similarity determination apparatus according to the second embodiment is the same as the configuration of the similarity determination apparatus illustrated in FIG. 2 except only the process to be performed. Therefore, the detailed description of the apparatus will not be repeated. The similarity determination apparatus according to the second embodiment differs from the similarity determination apparatus according to the first embodiment in that it further derives the similarity between the entire region of the examination image V0 and the entire region of the case image and determines the similarity between the examination image V0 and the case image, using the similarity (hereinafter, referred to as a first similarity) derived using the partial region P0 of the examination image V0 and the similarity (hereinafter, referred to as a second similarity) between the entire region of the examination image V0 and the entire region of the case image.

In the second embodiment, the finding classification unit 22, the feature amount calculation unit 23, and the weighting coefficient setting unit 24 classify the partial region P0 of the examination image V0 into findings, calculate the first feature amount for each finding, and set the weighting coefficient Wi corresponding to the size of the findings as in the first embodiment. In addition, it is assumed that the weighting coefficient set in the first embodiment is referred to as a first weighting coefficient W1$i$.

In the second embodiment, the finding classification unit 22 classifies each pixel in the entire region of the examination image V0 into at least one of a plurality of types of findings. The feature amount calculation unit 23 calculates the feature amount for each of the findings classified in the examination image V0. In addition, it is assumed that the feature amount calculated for the entire region of the examination image V0 is referred to as a third feature amount. Further, the weighting coefficient setting unit 24 sets, as a second weighting coefficient W2$i$, a weighting coefficient indicating the degree of weighting, which varies depending on the size of each finding, for each finding classified into the examination image V0.

Here, the processes performed by the finding classification unit 22, the feature amount calculation unit 23, and the weighting coefficient setting unit 24 in the second embodiment are the same as the processes performed by the finding classification unit 22, the feature amount calculation unit 23, and the weighting coefficient setting unit 24 using the partial region P0 of the examination image V0 in the first embodiment except that the entire region of the examination image V0 is used. Therefore, the detailed description thereof will not be repeated here.

In the second embodiment, first, the similarity derivation unit 25 derives the region similarities between the partial region P0 of the examination image V0 and the small regions A1 to A8 of the case image and derives a representative region similarity among the plurality of region similarities as a first similarity Sf1 between the examination image V0 and the case image as in the first embodiment. In addition, the similarity derivation unit 25 performs a weighting operation for the third feature amount for each finding calculated in the examination image V0 and the feature amount (hereinafter, referred to as a fourth feature amount) for each finding calculated in advance in the case image on the basis of the second weighting coefficient W2$i$ set by the weighting coefficient setting unit 24 to derive a second similarity Sf2 between the examination image V0 and the case image. Then, as represented by the following Expression (10), the similarity derivation unit 25 weights the first similarity Sf1 and the second similarity Sf2 using a weighting coefficient α and adds the similarities to derive a final similarity Sf0 between the examination image V0 and the case image.

$$Sf0 = \alpha \times Sf1 + (1-\alpha) \times Sf2 \quad (10)$$

Here, in a first case in which emphysema and a nodule as a lesion are included and in a second case in which a nodule is included as a lesion in a normal lung, the shape of the lesion in the first case may be different from the shape of the lesion in the second case due to the influence of emphysema even in a disease such as a nodule. Further, for treatment, it is necessary to perform the treatment in consideration of emphysema in the first case. Here, emphysema is a finding that appears in the entire region of the lung. Therefore, it may be desired to search for case images in consideration of not only a local region of the lung but also the entire region of the lung.

In the second embodiment, in addition to the first similarity Sf1 derived in the first embodiment, the second similarity Sf2 is derived in consideration of the entire region of the examination image V0 to derive the similarity between the examination image V0 and the case image. Therefore, it is possible to search for case images similar to the examination image V0 in consideration of diseases in the entire region of the lung.

Figure 14:
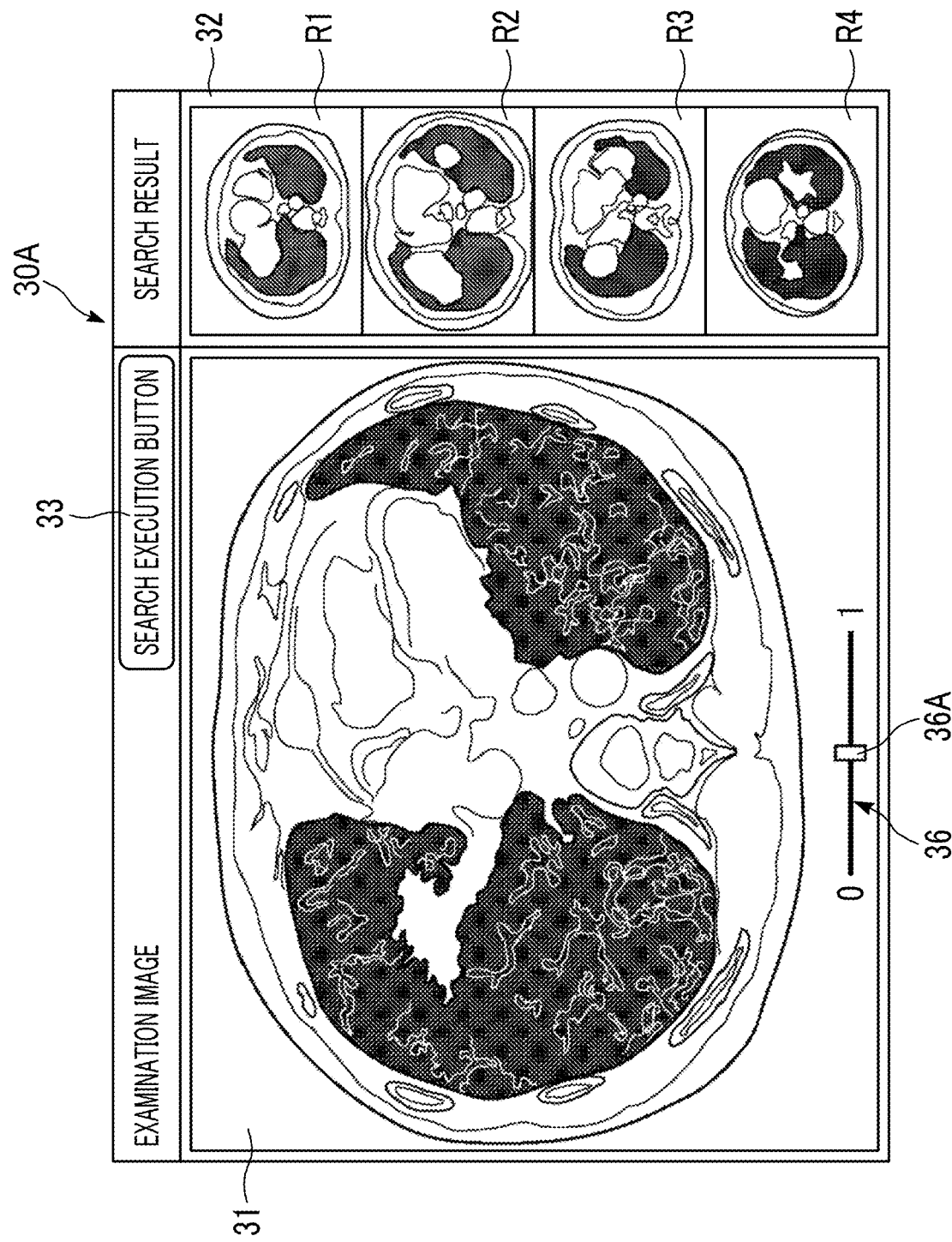
FIG. 14 is a diagram illustrating the search results in which a slider is displayed.

Further, in the second embodiment, the value of the weighting coefficient α in Expression (10) may be changed. FIG. 14 is a diagram illustrating a search result display screen in the second embodiment. As illustrated in FIG. 14, a slider 36 is displayed on a search result display screen 30A in the second embodiment. In the slider 36, a knob 36A can be moved to the left and right by the input unit 15 to change the weight coefficient α in Expression (10). In accordance with the above, the configuration in which the weighting coefficient α in Expression (10) can be changed makes it possible to change the degree of importance of the partial region P0 of the examination image V0 or the degree of importance of the entire region. Therefore, the user can search for a desired case image.

Figure 15:
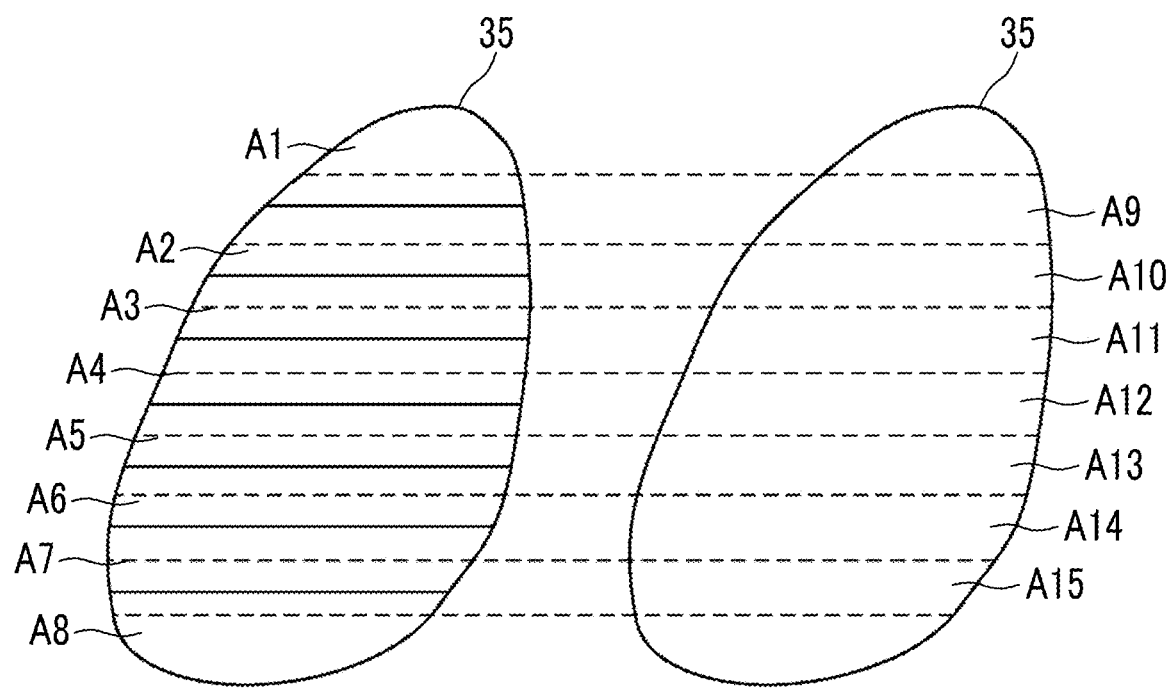
FIG. 15 is a diagram illustrating a state in which the lung region of the case image is divided into small regions that overlap each other.

Further, in the first and second embodiments, the lung region of the case image is divided into, for example, eight small regions. However, in the division of the lung region into small regions, in a case in which a finding similar to the finding included in the partial region P0 of the examination image V0 is present at the boundary between the small regions, the similarity between the partial region P0 and the small region is reduced. Therefore, in a case in which the case image is divided into small regions, it is preferable to divide the case image into a plurality of small regions having overlapping regions. FIG. 15 is a diagram illustrating a state in which a case image is divided into a plurality of small regions having overlapping regions. FIG. 15 illustrates a state in which the lung region 35 of the case image is divided into the eight small regions A1 to A8 illustrated in FIG. 8 and is divided into seven small regions A9 to A15 that overlap the small regions A1 to A8 as illustrated on the right side in FIG. 15.

In accordance with the above, since the case image is divided into a plurality of small regions having overlapping regions, findings are located at positions away from the boundaries between the small regions A1 to A8 in the small regions A9 to A15 even in a case in which the findings are present at the boundaries between the small regions A1 to A8. On the contrary, even in a case in which the findings are present at the boundaries between the small regions A9 to A15, the findings are present at positions away from the boundaries between the small regions A9 to A15 in the small regions A1 to A8. Therefore, it is possible to derive the similarities between the partial region P0 and the small regions of the case image with high accuracy.

Figure 16:
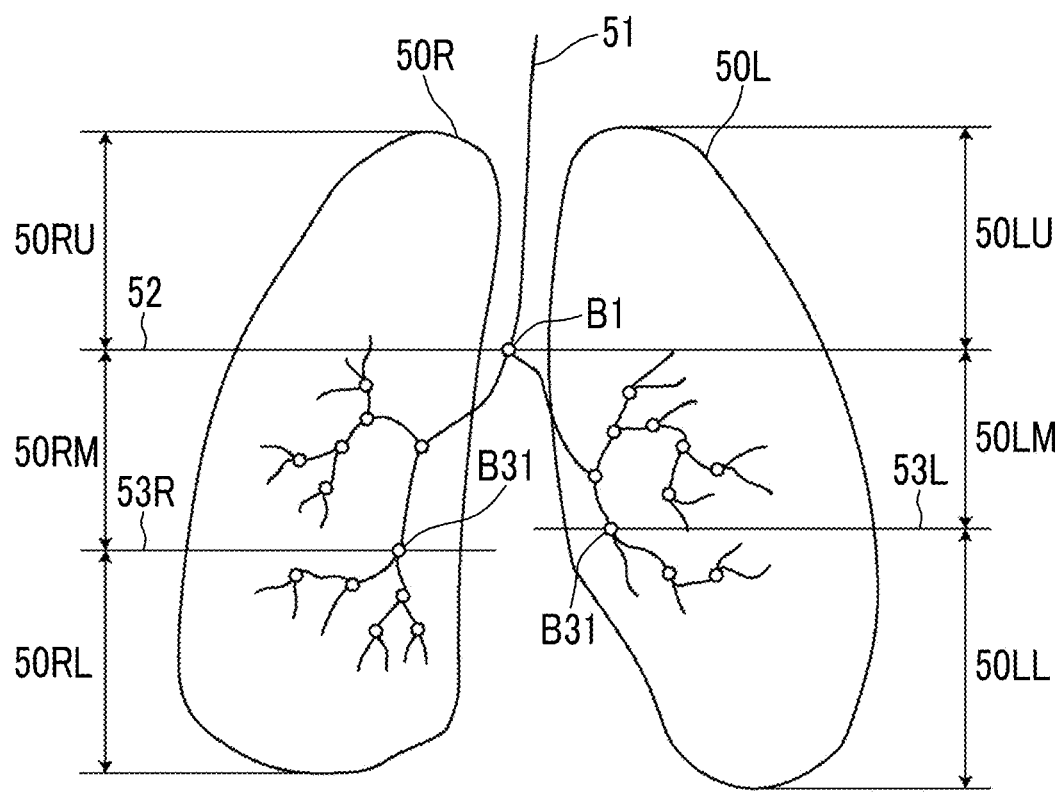
FIG. 16 is a diagram illustrating the division of the lung region into other small regions.

Further, in the first and second embodiments, the lung region of the case image is divided into equal parts. However, the present disclosure is not limited thereto. For example, the lung region may be divided into three regions of upper, middle, and lower regions on the basis of a first bronchial branch and a third bronchial branch among the branch positions of the bronchus, and each of the upper, middle, and lower regions may be further divided into equal parts by volume. FIG. 16 is a diagram illustrating the division of the lung region using the branch positions of the bronchus. In addition, the first bronchial branch corresponds to a branch point between the trachea and the left and right bronchi. In this embodiment, it is assumed that the branches from the first bronchial branch to the distal end of the bronchus are referred to as a second bronchial branch, a third bronchial branch, and so on. Two third bronchial branches are present in each of the left and right lung regions. In this embodiment, it is assumed that region division is performed on the basis of the third bronchial branches located on the lower side in the direction of the body axis of the subject. As illustrated in FIG. 16, in a case in which the lung region is divided, a horizontal plane 52 is set at a first bronchial branch Bi, and horizontal planes 53L and 53R are set at third bronchial branches B31 on the lower side in the left and right lung regions 50L and 50R, respectively. Further, in FIG. 16, the lung region is two-dimensionally illustrated. However, since the case image is a three-dimensional image, in practice, the horizontal planes are set as described above. Here, the horizontal plane means a plane perpendicular to the body axis of the subject whose case image has been acquired.

In addition, the left lung region 50L is divided into three regions of a left upper lung region 50LU between the horizontal plane 52 and the upper end of the left lung region 50L, a left middle lung region 50LM between the horizontal plane 52 and the horizontal plane 53L, and a left lower lung region 50LL between the horizontal plane 53L and the lower end of the left lung region 50L. Further, the right lung region 50R is divided into three regions of a right upper lung region 50RU between the horizontal plane 52 and the upper end of the right lung region 50R, a right middle lung region 50RM between the horizontal plane 52 and the horizontal plane 53R, and a right lower lung region 50RL between the horizontal plane 53R and the lower end of the right lung region 50R. Furthermore, each of the left and right upper lung regions 50LU and 50RU and the left and right middle lung regions 50LM and 50RM is divided into three equal parts, and each of the left and right lower lung regions 50LL and 50RL is divided into five equal parts. Moreover, the number of divisions of each of the left and right upper lung regions 50LU and 50RU, the left and right middle lung regions 50LM and 50RM, and the left and right lower lung regions 50LL and 50RL is not limited to the above. Since the lower lung region is usually large in the lung, it is preferable that the number of divisions of the lower lung region is larger than that of the upper lung region and the middle lung region.

This division of the lung region makes it possible to derive the similarities between the partial region P0 of the examination image V0 and the small regions of the case image in consideration of the partial swelling and atrophy of the lung region.

Figure 17:
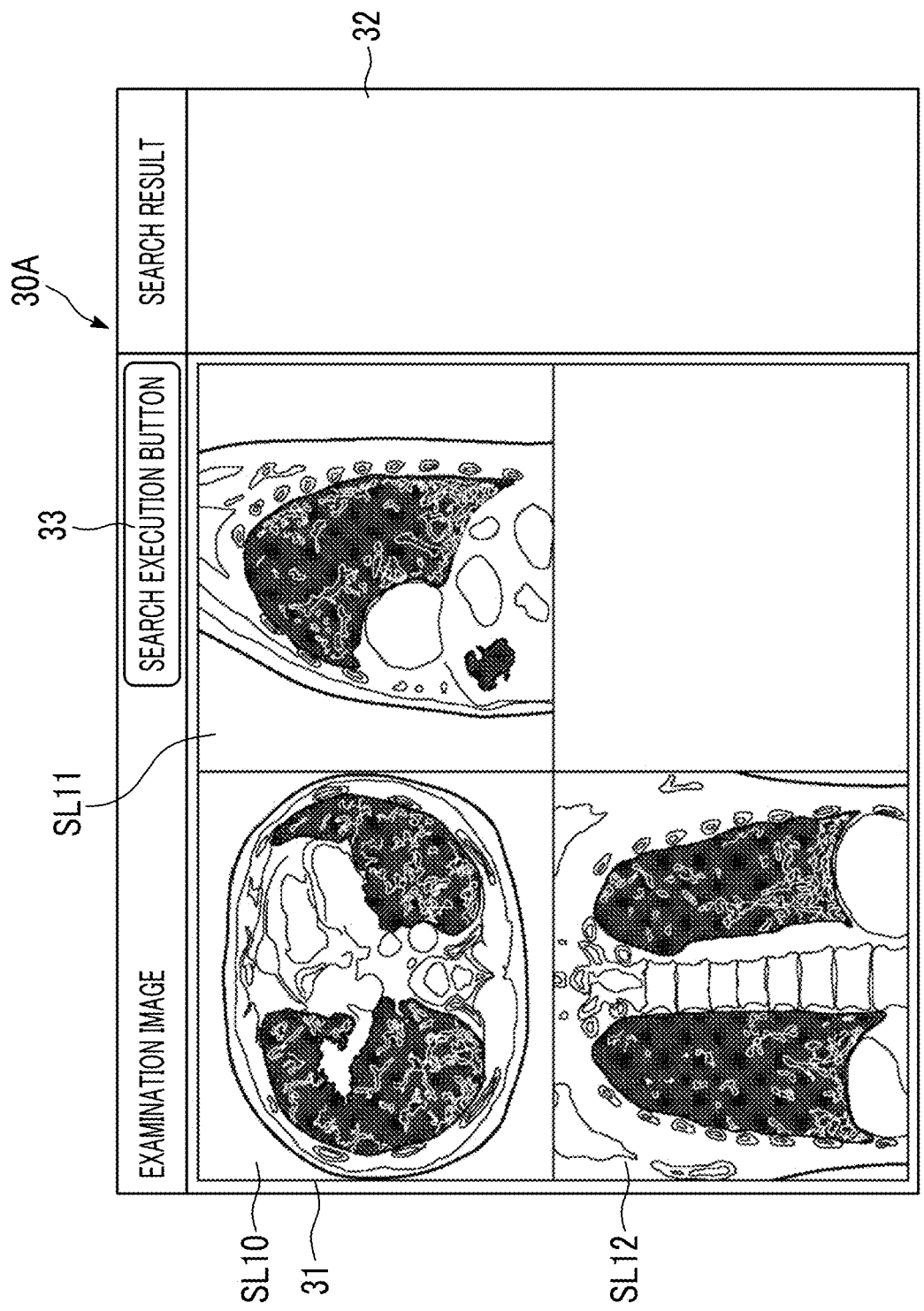
FIG. 17 is a diagram illustrating a state in which tomographic images in the directions of three axes are displayed.
Figure 18:
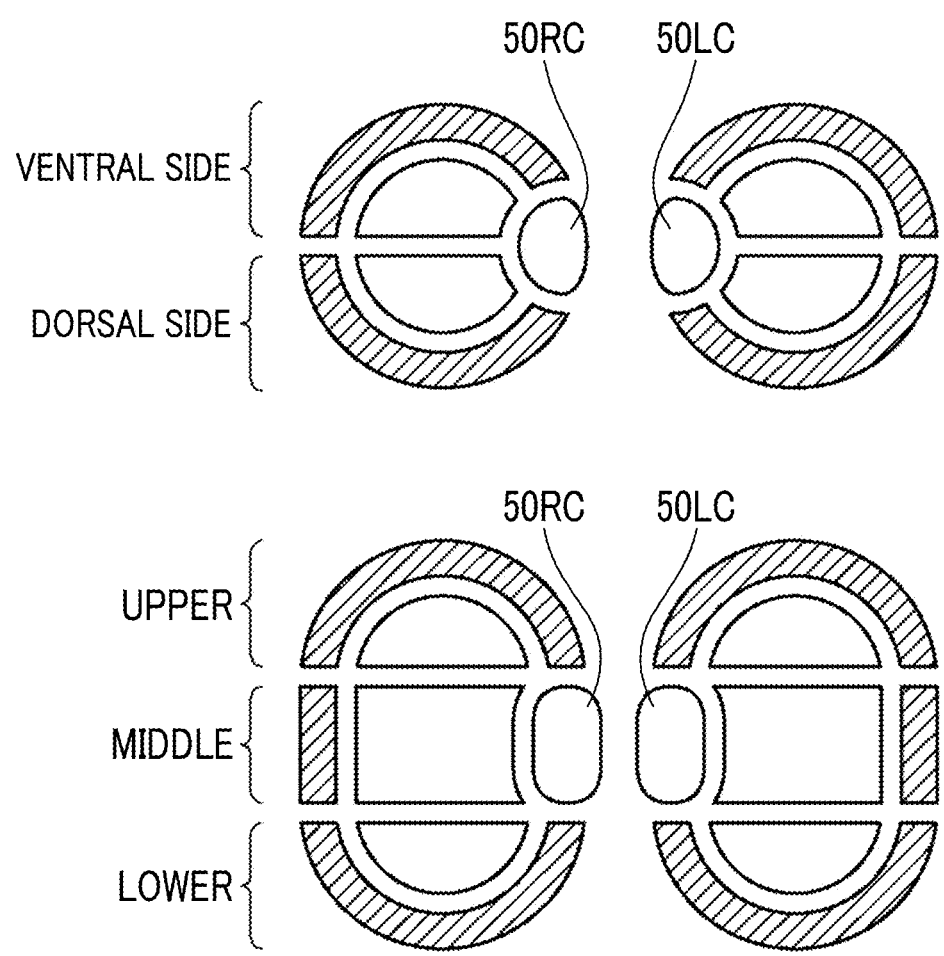
FIG. 18 is a diagram illustrating the division of the lung region into other small regions.

Further, in the above-described embodiments, the tomographic image of one tomographic plane of the examination image V0 is displayed. However, the present disclosure is not limited thereto. As illustrated in FIG. 17, the examination slice image display region 31 may be divided into three small display regions, and an examination slice image SL10 of the axial cross section, an examination slice image SL11 of the sagittal cross section, and an examination slice image SL12 of the coronal cross section in the examination image V0 may be displayed in each small display region. Here, the intersection lines of the three examination slice images intersect each other at one point. Therefore, the partial region P0 of the examination image V0 may be a region including the intersection point of the three examination slice images. In this case, the lung region of the examination image V0 may be divided as follows, and the region including the intersection point may be used as the partial region P0. That is, as illustrated in FIG. 18, the left and right lung regions are divided into a left central region 50LC, a right central region 50RC, and other regions, and the regions other than the central region are further divided into three regions of upper, middle, and lower regions, intermediate and outer regions, and ventral and dorsal sides. In FIG. 18, the outer region is hatched. In this case, each of the left and right lung regions is divided into 13 regions.

Further, in the above-described embodiments, the partial region P0 including the tomographic plane of the examination slice image displayed in the examination slice image display region 31 is set in the examination image V0. However, the present disclosure is not limited thereto. Similarly to the case image, the examination image V0 may be divided into a plurality of small regions in advance, and the small region including the tomographic plane of the examination slice image may be used as the partial region P0. In this case, it is preferable to calculate the first feature amount in advance in each of the small regions of the examination image V0. This makes it possible to reduce the calculation time for deriving the similarity between the examination image V0 and the case image. Therefore, it is possible to search for similar case images at high speed. In addition, the examination image V0 may be divided into a plurality of small regions that overlap each other as illustrated in FIG. 15.

Further, in the above-described embodiments, the tomographic image of the examination image V0 is displayed on the display unit 14. However, the present disclosure is not limited thereto. The finding classification unit 22 may generate a mapping image of the examination image V0, and the tomographic image of the mapping image may be displayed on the display unit 14.

That is, a mapping image may be generated by assigning colors to each classified region in the partial region P0 on the basis of the result of the finding classification process of the finding classification unit 22, and the generated mapping image may be displayed. Specifically, the finding classification unit 22 assigns the same color to the pixels classified into the same finding for all of the pixels in a three-dimensional space classified into any of the plurality of types of findings to generate a three-dimensional mapping image. FIG. 19 is a diagram illustrating one tomographic plane of the mapping image in which colors corresponding to a plurality of types of classifications are assigned to the classifications. In addition, FIG. 19 illustrates the mapping image in a case in which the pixels are classified into eight types of findings, that is, a ground-glass shadow, a normal lung, bronchodilatation, a honeycomb lung, a reticular shadow, an infiltrative shadow, a low absorption area, and a cyst for simplicity of description. Further, FIG. 19 illustrates only the mapping image of one lung.

Further, in each of the above-described embodiments, a plurality of evaluation values indicating the possibility of each pixel of the examination image V0 being each of a plurality of types of findings are calculated for each pixel, and each pixel of the examination image V0 is classified into at least one of the plurality of types of findings on the basis of the plurality of evaluation values. However, a finding classification method is not limited to the method using the evaluation values.

In addition, in each of the above-described embodiments, the case database DB is stored in the image storage server 3. However, the case database DB may be stored in the storage 13.

Further, in each of the above-described embodiments, the examination image is registered in the case database DB. However, images other than the examination image may be registered as registration target images in the case database.

In each of the above-described embodiments, for example, the following various processors can be used as the hardware structure of processing units performing various processes, such as the image acquisition unit 20, the display control unit 21, the finding classification unit 22, the feature amount calculation unit 23, the weighting coefficient setting unit 24, the similarity derivation unit 25, and the search unit 26. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). In accordance with the above, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A similarity determination apparatus that determines a similarity between a first three-dimensional medical image and a second three-dimensional medical image, the similarity determination apparatus comprising at least one processor, wherein the processor is configured to:
   display a tomographic image of a specific tomographic plane in the first medical image on a display;
   classify each pixel of a partial region including at least the specific tomographic plane in the first medical image into at least one of a plurality of types of findings;
   calculate a first feature amount for each finding classified in the partial region;
   set a weighting coefficient indicating a degree of weighting, which varies depending on a size of each finding, for each finding classified in the partial region; and
   perform a weighting operation for the first feature amount for each finding calculated in the partial region and a second feature amount for each finding calculated in the second medical image on the basis of the weighting coefficient to derive the similarity between the first medical image and the second medical image.

2. The similarity determination apparatus according to claim 1,
   wherein the processor is configured to derive region similarities between the partial region and each of a plurality of small regions in the second medical image and determine a representative similarity among the plurality of region similarities as the similarity between the first medical image and the second medical image.

3. The similarity determination apparatus according to claim 2,
   wherein the processor is configured to increase a region similarity for a small region that is positionally closer to the partial region among the plurality of small regions and determine the representative similarity.

4. The similarity determination apparatus according to claim 2,
   wherein the second medical image is divided into the plurality of small regions having overlapping regions.

5. The similarity determination apparatus according to claim 1,
   wherein the first medical image is divided into a plurality of small regions, the first feature amount is calculated in each of the plurality of small regions, and the weighting coefficient is set in each of the plurality of small regions, and
   the processor is configured to use the small region including the specific tomographic plane as the partial region and perform the weighting operation for the first feature amount for each finding calculated in the partial region and the second feature amount for each finding calculated in the second medical image on the basis of the weighting coefficient to derive the similarity between the first medical image and the second medical image.

6. The similarity determination apparatus according to claim 1,
   wherein the processor is configured to include a discriminator that has been subjected to machine learning so as to classify the plurality of types of findings and classify each pixel of the partial region into the plurality of types of findings using the discriminator.

7. The similarity determination apparatus according to claim 1,
   wherein the processor is configured to:
   classify each pixel of the first medical image into at least one of the plurality of types of findings;
   calculate a third feature amount for each finding classified in the first medical image;
   set, as a first weighting coefficient, the weighting coefficient indicating the degree of weighting, which varies depending on the size of each finding, for each finding classified in the partial region and set, as a second weighting coefficient, a weighting coefficient indicating a degree of weighting, which varies depending on the size of each finding, for each finding classified in the first medical image, and
   perform the weighting operation for the first feature amount for each finding calculated in the partial region and the second feature amount for each finding calculated in the second medical image on the basis of the first weighting coefficient to derive the similarity between the first medical image and the second medical image as a first similarity, perform a weighting operation for the third feature amount for each finding calculated in the first medical image and a fourth feature amount for each finding calculated in the second medical image on the basis of the second weighting coefficient to derive a similarity between the first medical image and the second medical image as a second similarity, and derive a final similarity between the first medical image and the second medical image on the basis of the first similarity and the second similarity.

8. The similarity determination apparatus according to claim 7,
wherein the processor is configured to weight and add the first similarity and the second similarity to derive the final similarity.

9. The similarity determination apparatus according to claim 8,
wherein the processor is capable of changing a weighting coefficient in a case in which the first similarity and the second similarity are weighted and added.

10. The similarity determination apparatus according to claim 7,
wherein the processor is further configured to search for the second medical image similar to the first medical image as a similar medical image on the basis of the final similarities between the first medical image and a plurality of second medical images with reference to a case database in which the plurality of second medical images are registered and the second and fourth feature amounts for each of the plurality of second medical images are registered so as to be associated with each of the plurality of second medical images.

11. The similarity determination apparatus according to claim 1,
wherein the processor is configured to search for the second medical image similar to the first medical image as a similar medical image on the basis of similarities between the first medical image and a plurality of second medical images with reference to a case database in which the plurality of second medical images are registered and the second feature amount for each of the plurality of second medical images is registered so as to be associated with each of the plurality of second medical images.

12. The similarity determination apparatus according to claim 11,
wherein, in a case in which the tomographic image of the specific tomographic plane is displayed for a predetermined time, the processor performs the search.

13. The similarity determination apparatus according to claim 11,
wherein the processor is configured to display a search result of the similar medical image on the display.

14. A similarity determination method that determines a similarity between a first three-dimensional medical image and a second three-dimensional medical image, the similarity determination method comprising:
displaying a tomographic image of a specific tomographic plane in the first medical image on a display;
classifying each pixel of a partial region including at least the specific tomographic plane in the first medical image into at least one of a plurality of types of findings;
calculating a first feature amount for each finding classified in the partial region;
setting a weighting coefficient indicating a degree of weighting, which varies depending on a size of each finding, for each finding classified in the partial region; and
performing a weighting operation for the first feature amount for each finding calculated in the partial region and a second feature amount for each finding calculated in the second medical image on the basis of the weighting coefficient to derive the similarity between the first medical image and the second medical image.

15. A non-transitory computer-readable storage medium that stores a similarity determination program that causes a computer to perform a process of determining a similarity between a first three-dimensional medical image and a second three-dimensional medical image, the similarity determination program causing the computer to perform:
a step of displaying a tomographic image of a specific tomographic plane in the first medical image on a display;
a step of classifying each pixel of a partial region including at least the specific tomographic plane in the first medical image into at least one of a plurality of types of findings;
a step of calculating a first feature amount for each finding classified in the partial region;
a step of setting a weighting coefficient indicating a degree of weighting, which varies depending on a size of each finding, for each finding classified in the partial region; and
a step of performing a weighting operation for the first feature amount for each finding calculated in the partial region and a second feature amount for each finding calculated in the second medical image on the basis of the weighting coefficient to derive the similarity between the first medical image and the second medical image.

* * * * *